United States Patent [19]
Takemoto et al.

[11] Patent Number: 5,984,780
[45] Date of Patent: Nov. 16, 1999

[54] IMAGE DISPLAY GAMING SYSTEM AND GAMING HOUSE MANAGEMENT SYSTEM

[75] Inventors: Takatoshi Takemoto; Masayuki Tsurumi, both of Tokyo, Japan

[73] Assignee: Kabushiki Kaisha Ace Denken, Kanagawa, Japan

[21] Appl. No.: 08/666,455

[22] PCT Filed: Oct. 17, 1994

[86] PCT No.: PCT/JP94/01744

§ 371 Date: Jun. 26, 1996

§ 102(e) Date: Jun. 26, 1996

[87] PCT Pub. No.: WO95/17935

PCT Pub. Date: Jul. 6, 1995

[30] Foreign Application Priority Data

| Dec. 27, 1993 | [JP] | Japan | 5-332046 |
| Dec. 27, 1993 | [JP] | Japan | 5-332047 |
| Dec. 27, 1993 | [JP] | Japan | 5-332048 |
| Dec. 27, 1993 | [JP] | Japan | 5-332049 |
| Apr. 14, 1994 | [JP] | Japan | 6-075715 |

[51] Int. Cl.$^6$ ............... A63F 9/22; A63F 7/00; G07F 17/34

[52] U.S. Cl. .............................. 463/20; 463/31

[58] Field of Search ............... 463/1, 25, 29, 463/30, 31, 36, 40–43; 364/410, 411, 412; 273/138.1, 138.2, 139; 235/380, 382; 382/100, 115

[56] References Cited

U.S. PATENT DOCUMENTS

| 4,467,335 | 8/1984 | Schmidt et al. . | |
| 4,521,014 | 6/1985 | Sitrick | 463/31 |
| 4,572,509 | 2/1986 | Sitrick | 463/31 |
| 4,593,936 | 6/1986 | Opel . | |
| 4,629,306 | 12/1986 | Warwick . | |
| 4,688,105 | 8/1987 | Bloch et al. . | |
| 4,710,873 | 12/1987 | Breslow et al. | 463/31 |
| 5,321,751 | 6/1994 | Ray et al. . | |
| 5,553,864 | 9/1996 | Sitrick | 463/31 |
| 5,595,389 | 1/1997 | Parulski et al. | 463/31 |

FOREIGN PATENT DOCUMENTS

| 63-22693 | 1/1988 | Japan . |
| 63-312896 | 12/1988 | Japan . |
| 1-190383 | 7/1989 | Japan . |
| 2-179079 | 7/1990 | Japan . |
| 3-275092 | 12/1991 | Japan . |
| 4-106593 | 4/1992 | Japan . |
| 4-106594 | 4/1992 | Japan . |
| 92-09344 | 6/1992 | Japan . |
| 4-205344 | 7/1992 | Japan . |
| 4-259480 | 9/1992 | Japan . |
| 4-303488 | 10/1992 | Japan . |
| 4-338477 | 11/1992 | Japan . |
| 4-354069 | 12/1992 | Japan . |
| 5-184 | 1/1993 | Japan . |
| 5-123441 | 5/1993 | Japan . |
| 6-135187 | 5/1994 | Japan . |

*Primary Examiner*—Valencia Martin-Wallace
*Assistant Examiner*—Mark A Sager
*Attorney, Agent, or Firm*—Seed and Berry LLP

[57] ABSTRACT

An image input section 1530 of a storage medium issuing system inputs image information and an image processing unit 420 performs image processing for the image information input through the image input section 1530. The image information processed by the image processing section is stored on a storage medium by an image write section 1500.

When the storage medium on which the image information is stored is inserted into a gaming machine, the image information is read by a read section of the gaming machine. A game execution section of the gaming machine executes a predetermined game in accordance with image information concerning the game stored in a game image storage section. A display control section controls display of the image information read from the storage medium instead of reading a specific symbol among the image information stored in the game image storage section. For example, appearances of a player are input as image information, whereby the input player's appearances can be displayed in place of the specific symbol.

13 Claims, 19 Drawing Sheets

Fig. 6

ROTATION SYMBOL TEMPLATE TABLES i) TEMPLATE TABLES OF ACCELERATION PATTERN ii) TEMPLATE TABLES OF CONSTANT SPEED PATTERN iii) TEMPLATE TABLES OF DECELERATION PATTERN iv) DATA CONFIGURATION OF TEMPLATE TABLE

| FLAG |
|---|
| (a) READ START POSITION |
| (b) NUMBER OF DATA BYTES |

SSDT01 ... SSDT21

CNDT01 ... CNDT14

SED00, SED03
SED10, SED13
SED20, SED23

STOP DISPENSING

NOTE: SSDT=SLOW START DATA
NOTE: CNDT=CONSTANT DATA
NOTE: SED=SLOW END DATA v) SSDT INDEX TABLE

| SSTBL: | SSDT0 |
|---|---|
| +2: | SSDT1 |
| --- | --- |
| +42: | SSDT21 |
| +44: | FF | vi) CNDT INDEX TABLE

| CNTL: | CNDT0 |
|---|---|
| +2: | CNDT1 |
| --- | --- |
| +28: | CNDT14 |
| +30: | FF | vii) SED INDEX TABLE

| SETBL0: | SED 00 |
|---|---|
| +2: | 01 |
| +4: | 02 |
| +8: | 03 |
| +10: | FF |

| SETBL1: | SED 10 |
|---|---|
| +2: | 11 |
| +4: | 12 |
| +8: | 13 |
| +10: | FF |

| SETBL2: | SED 20 |
|---|---|
| +2: | 21 |
| +4: | 22 |
| +8: | 23 |
| +10: | FF | viii) MOVE POINTER

| INDEX TABLE ACCESS POSITION | SEQUENTIAL COUNTER OF DISPLAY TEMPLATE POSITION OF EACH DISPLAY WINDOW |
|---|---|

```
                                              1994.9.30
                                    PRESENT TIME 16:00
```
| GAME PLAY TIME | 10A GAMING MACHINE | USE CONDITIONS | | ABNORMAL CONDITION FLAG |
|---|---|---|---|---|
| | | NO. OF INPUT BALLS | NO. OF OUTPUT BALLS | |
| 10:00~12:00 | 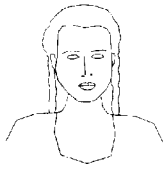 | 1000 | 200 | |
| 12:20~12:30 |  | 100 | 50 | |
| 14:00~15:05 |  | 1500 | 500 | |
| 15:55~ |  | 100 | 3000 | ABNORMAL CONDITION |
*Fig. 20*

| GAMING MACHINE NO. | IMAGE NO. | NUMBER OF INPUT BALLS | NUMBER OF OUTPUT BALLS | START TIME | END TIME | ABNORMAL CONDITION FLAG |
|---|---|---|---|---|---|---|
| 10A | 100 | 1000 | 200 | 10:00 | 12:00 | — |
| 10A | 101 | 100 | 50 | 12:20 | 12:30 | — |
| 10A | 102 | 1500 | 500 | 14:00 | 15:05 | — |
| 10A | 103 | 100 | 3000 | 15:55 | | ON |
| ... | ... | ... | ... | ... | ... | |

MANAGEMENT TABLE 2210

*Fig. 23*

IMAGE DISPLAY GAMING SYSTEM AND GAMING HOUSE MANAGEMENT SYSTEM

TECHNICAL FIELD

This invention relates to a gaming machine and in particular to an image display gaming machine comprising an image display control section for controlling image display or an image display section.

TECHNICAL BACKGROUND

For example, video game machines, slot machines, pachinko (Japanese pinball) machines, etc., are available as gaming machines for controlling image display for playing games. Character and background images are controlled with the video game machines, and symbol pattern display is controlled with the slot machines and pachinko machines.

Hitherto, such gaming machines have utilized image data previously stored as game software for the images displayed in the games. Thus, when repeating games more than once, the player may get tired of the same screen and lose interest in the games.

To solve this problem, an technique for enabling a player to change the appearances of characters displayed on a screen, and the background, as he or she desires, is disclosed in Japanese Patent Laid-Open No. Hei 4-259480. In the related art, an image of a person is captured with a television camera, and an image signal of the person is converted into image data by AD conversion means. Image data in game software stored in a memory is read, the image data portion corresponding to the area where a person would be displayed is discriminated from the image data and erased, and the image data from the AD conversion means is edited and assigned to the erased image data. At this time, the player specifies the image type (person or background) by pushing a push button on the television camera, whereby an image type signal is output.

In the related art, the positional relationship between the television camera and object and image processing are not discussed in detail. For example, image processing may become complicated for replacing the image data in game software depending on the size of the object captured with the television camera. The image taking-in time and the switching time into image of appearances are not particularly considered.

DISCLOSURE OF INVENTION

It is therefore an object of the invention to provide an image display gaming system which enables a player to have a sense of taking part in a game and to enjoy playing a game. It is another object of the invention to provide an image display gaming system which can perform image processing and a gaming house management system.

To these ends, according to the invention, there is provided an image display gaming system comprising:
  a storage medium issuing system comprising image pickup means for picking up an image of an object and inputting image information, image processing means for performing image processing for image information of the image picked up by the image pickup means, write means for writing the image information processed by the image processing means onto a storage medium, and issuing means for issuing the storage medium on which the image information is written by the write means;
  a storage medium onto which the image information is written;
  a plurality of gaming machines each comprising an insertion section through which the storage medium is inserted, a read section for reading the image information from the storage medium inserted through the insertion section, a game execution section for executing a game, and a display control section for controlling display of image information concerning games;
  a display unit being controlled by the display control section of the gaming machine; and
  a game image storage for storing the image information concerning games, wherein
  the display control section can read the image information stored on the storage medium read by the read section and the image information stored in the game image storage and perform display control.

A storage medium issuing system for issuing storage media used in a gaming house may comprise:
  image pickup means for picking up an image of an object for inputting image information;
  image processing means for performing image processing using image information of the image picked up by the image pickup means to obtain a specific size of image information;
  write means for writing the image information processed by the image processing means into a predetermined area of the storage medium; and
  issuing means for issuing the storage medium on which the image information is written by the write means.

The function of such means is described below:

In the storage medium issuing system, the image pickup means such as a CCD camera having an automatic focusing function picks up an image of an object for inputting image information. The image processing means performs image processing for the image information of the image picked up by the image pickup means. The write means writes the image information processed by the image processing means onto the storage medium. The issuing means issues the storage medium on which the image information is written by the write means.

A player inserts the storage medium on which the image information is written into the insertion section of the gaming machine.

In the gaming machine, the read section reads the image information from the storage medium inserted in the insertion section. The game execution section executes a game. The display control section reads the image information stored in the game image storage and the image information stored on the storage medium and performs display control, whereby the image information stored in the game image storage and the image information stored on the storage medium are displayed on the display unit.

The storage medium issuing system can further include display means for displaying the image information processed by the image processing means on the storage medium as visible information. For example, a player's appearances can be displayed on the surface of the storage medium. The storage medium can use a recyclable card which is a reusable storage medium, on which information can be recorded and erased visually.

The storage medium issuing system further includes a display section for displaying the image information and a print section, whereby a player can check the image information of the picked-up image.

Thus, the player can have a sense of taking part in a game and can enjoy playing a game.

Further, to use input image information for a security system, according to the invention, there is provided a gaming house management system comprising:

a plurality of gaming machines each comprising a game execution section for executing a game, a game image storage section for storing image information concerning games, an image input section for inputting image information from an image information source from which image information can be output, an image processing section for performing image processing for image information input through the image input section, and a sending section for sending out the image information processed by the image processing section; and a management system comprising a reception section for receiving image information from the sending sections of the gaming machines and a display section for displaying the image information received by the reception section.

In this case, each of the gaming machines further includes a detection section for detecting an illegal act perpetrated at the gaming machine and if the detection section detects an illegal act, the sending section of the gaming machine having the detection section informs the management system that the illegal act has been detected, the reception section of the management system further receives the information indicating detection of the illegal act from the sending section, and when the reception section receives the information indicating detection of the illegal act, the display section can display the information on where the illegal act was performed, together with the identification information of the gaming machine If such means is provided, input image information is sent from the sending sections of the gaming machines and the management system can receive and display the image information. When the detection section detects an illegal act, the information indicating detection of the illegal act can be displayed together with the identification information of the gaming machine at which the illegal act is detected and image information of the player at the gaming machine, whereby the gaming house can identify the player performing the illegal act.

BRIEF DESCRIPTION OF THE DRAWINGS

FIG. 6 is an illustration of the template configuration in the embodiment;

FIGS. 18 to 21 are illustrations showing screen examples of a management system when the invention is applied to the security system in the embodiment.

FIG. 23 is an illustration of a management table when the invention is applied to the security system in the embodiment.

BEST MODE FOR CARRYING OUT THE INVENTION

Referring now to the accompanying drawings, there are shown embodiments of the invention.

The invention can be applied to gaming machines for controlling image display, such as slot machines, pachinko machines, and video game machines. In an embodiment of the invention, slot machines will be discussed. In the embodiment, an image input section for inputting an image is placed in the main unit of a slot machine, the appearances of a player is captured and taken into the slot machine, and after image processing is performed, image information of the captured appearance is displayed in place of a specific symbol pattern.

Figure 1:
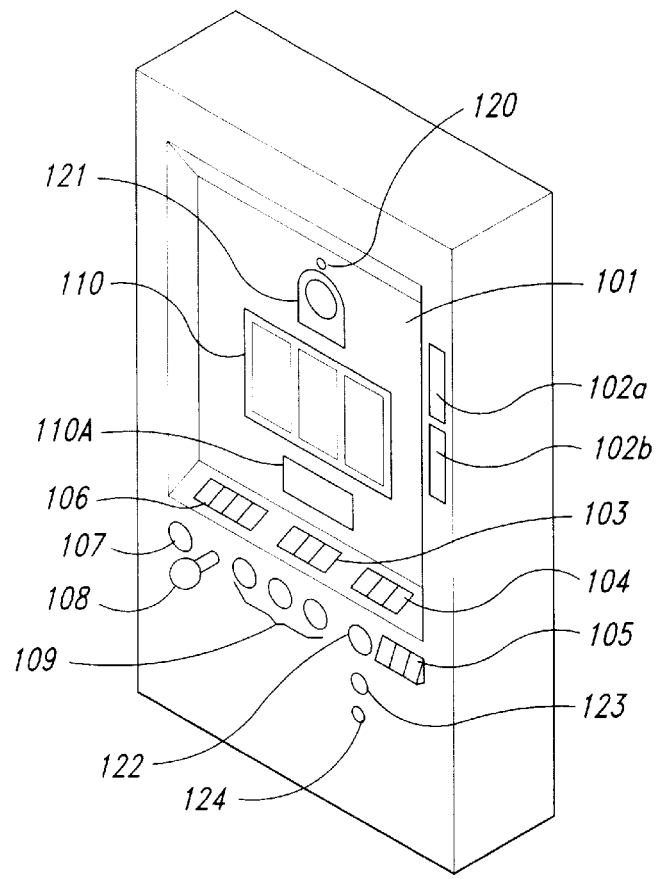
FIG. 1 is an external view of a slot machine in an embodiment.

FIG. 1 is an external view of the slot machine in the embodiment, wherein a display section 110 can be placed on a game board 101. The display section 110 is display means such as a CRT or liquid crystal display; a plurality of display windows for showing one or more rows of various symbols at the slot machine are displayed and a background can be displayed on the outside of each display window. The display section 110 displays a plurality of symbol rows as with conventional rotating drums and can move and change the symbols in sequence for changing and displaying the symbols as if they had rotated. It may comprise display means for each row. When a player plays a game, the display section 110 may display a win combination line and when the symbol combination matches a predetermined complete symbol pattern, may display information indicating the event. A CCD (Charged Coupled Device) camera section 121, as means for picking up the image of an object, and illumination means 120, such as a flash, are placed on the game board 101 for enabling the appearances of a player, etc., to be captured and input. A second display section 110A for displaying image information of an object captured with the camera section 121, and a display control section for causing the second display section to display it, may be provided in addition to the display section 110 for displaying image information.

An input/output section 102 can comprise an input/output section 102a for inputting medals, balls, bills, and coins used with normal slot machines, or the amount of money and the number of medals, and an input/output section 102b for inputting/outputting gaming storage media for playing games, such as IC cards, FD (floppy disk), and CD-ROM storing image information, etc., described below. A number-of-won-media display section 103 is display means for displaying the number of game play media paid out to the player for a winning game play, which will be hereinafter referred to as the number of won media, or the number paid out to the player for a winning game play, such as the amount of money when the symbols on the slot machine are complete as predetermined symbols. A number-of-taken-in-media-for-gaming display section 104 is display means for displaying the number of game play media or the amount of money input through the input/output section 102a. A taken-in-media-for-gaming selection switch 105 is a specification switch for a player to specify the number of game play media or an amount of money for a bet when playing a game. For example, if there are a plurality of betting lines indicating a plurality of symbol combinations, the player can use the switch for specification so that the betting line can be set in response to the number of medals. A number-of-internally-held-media display section 106 is display means for displaying the number of game play media or the amount of money, etc., held in the slot machine if the number of won media is not output. A settlement switch 107 is a specification switch for specifying settlement of the number of game play media held in the slot machine at the end of the game. For example, if the settlement switch 107 is pressed, as many game play media as held in the slot machine are output, or when a card comprising storage means is used, the number held in the slot machine can be stored on the card and this card can be dispensed. A start lever 108 is specification means for accepting a start instruction for rotation display of symbols on the slot machine. Game stop switches 109, which are provided in one-to-one correspondence with the rows, are specification means for accepting a game stop instruction. When a game stop instruction is accepted through one of the game stop switches 109, the corresponding symbol change is stopped at predetermined stop timing. It may be adapted to stop naturally after a lapse of a predetermined time after rotation display starts, without providing the game stop switches 109. Further, only one game stop switch 109 may be provided without being provided in one-to-one correspondence with the rows, and upon acceptance of a stop instruction through the game stop switch 109, the symbol changes may be stopped in a predetermined order.

Next, the detailed internal configuration in the embodiment will be discussed with reference to FIG. 4, which is a block diagram of a display-type slot machine.

Figure 4:
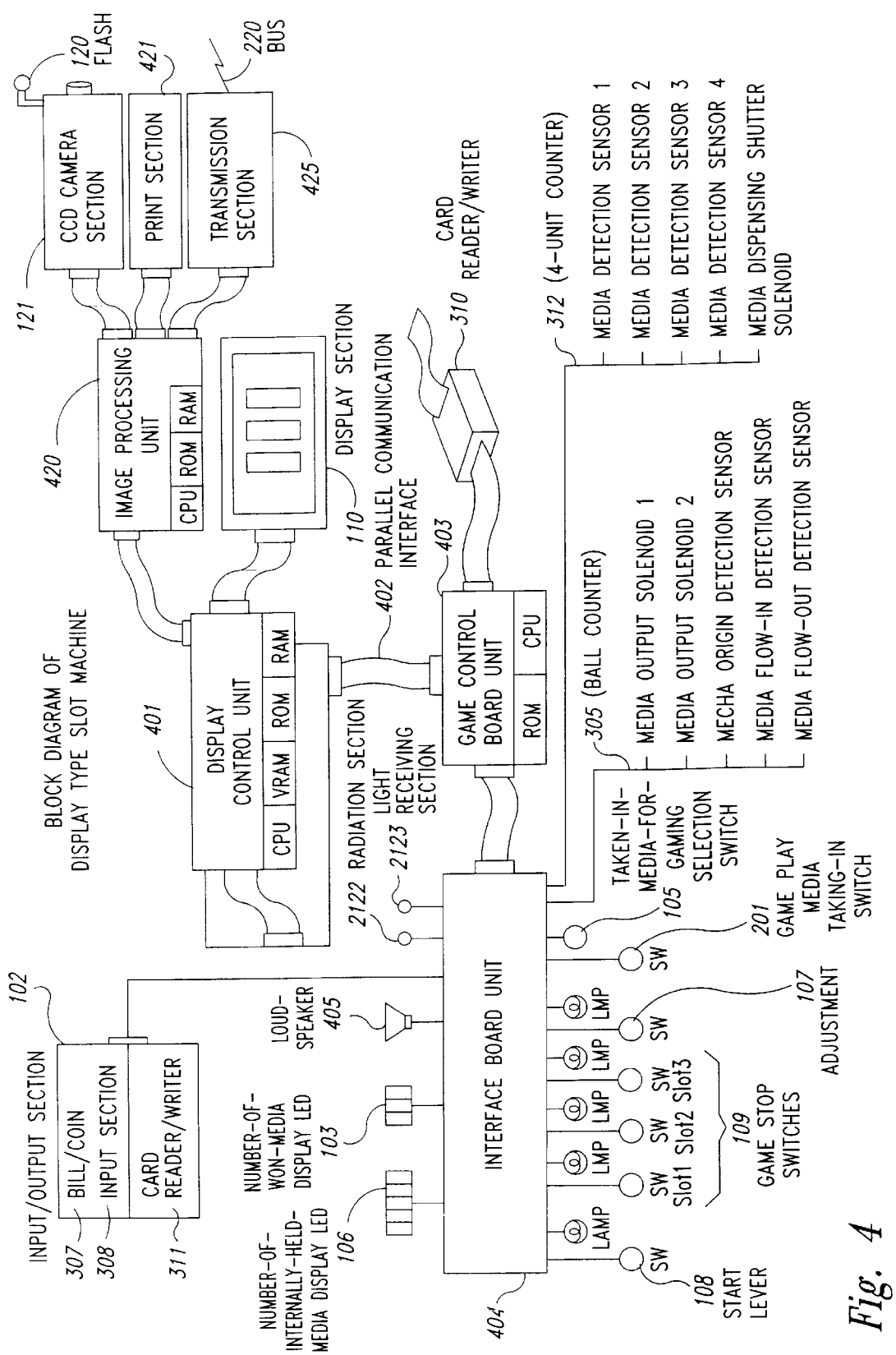
FIG. 4 is a block diagram of a slot machine in the embodiment.

In FIG. 4, the slot machine comprises a game control unit 403 for controlling game progress, a display control unit 401 for simulating a slot rotation state, an interface board unit 404 connected to various input/output units, a CCD (Charged Coupled Device) camera section 121 as means for picking up the image of an object, which is an image input unit for inputting an image, an image processing unit 420 for processing an image input through the CCD camera section 121 and outputting image information to the display control unit 401, and a display section 110 for displaying symbols and backgrounds. In FIG. 4, the game control unit 403 and the display control unit 401 are separate units each having a CPU. The slot machine may further include a print section 421 such as a printer being connected to the image processing unit 420 for printing out input image information. The game control unit 403 may comprise a card reader/writer 310 for reading/writing a card of a storage medium for storing image information. Image information input through another image input unit can be previously stored on the card, and when a player plays a game, the card can be mounted on the card reader/writer 310 for reading the image information. Further, information such as the number of game play media may be written onto the card.

The interface board unit 404, to which the input/output section 102, the specification switches, the display means, etc., are connected, is controlled by the game control unit 403. The specification switches comprise at least the start lever 108 of start instruction means for accepting a game start instruction and instructing the display control unit 401 to change symbol display for each row and the stop instruction means 109 for accepting a stop instruction for stopping the symbol change for each row and instructing the display control unit 401 to stop the symbol change. The slot machine may further include a loudspeaker 405 for producing a sound when symbols are complete, etc.

In addition to the CCD camera section 121, a still-video camera, a television camera, etc., may be used as the image pickup means; a color camera may be used. Further, an image may be read by a scanner, etc., as an image input section. Further, image information may be transmitted via a communication line for input. A storage medium for storing image information may be inserted into the input/output section 102b for reading the image information from the storage medium. The CCD camera section 121 inputs an image at a specific time and sends the input image to the image processing unit 420. It is placed on the game board of the slot machine as shown in FIG. 1, and can previously focus on the player's position when he or she plays a game. For example, if a chair or the like is provided in front of the slot machine, focusing can be previously obtained at a position when the player sits on the chair. The CCD camera section 121 may be provided with an automatic focusing function. The slot machine may further include illumination means 120, such as a flash being connected to the CCD camera section 121, for illuminating an object. The image taking-in time in the CCD camera section 121 will be discussed later. The image processing unit 420 processes image information input through the CCD camera section 121 and outputs the processed image information to the display control unit 401. The image processing unit 420 processes the input image information to a predetermined information size and sends the resultant image information. If the size of information input through the CCD camera section 121 is fixed, the image information may be sent to the display control unit 401 as it is.

In the entire system operation, the game control unit 403 controls game progress centrally in accordance with a program stored in a ROM, and transmits slot rotation and stop instructions to the display control unit 401 via a parallel communication interface 402, thereby effecting game progress. When slot rotation stops, the game control unit 403 determines whether the combination of the symbols displayed at predetermined positions of the display means matches a predetermined symbol combination. To display symbols as if they had rotated, the display control unit 401 stores various symbol patterns in a ROM and background pictures in a VRAM (Video Random Access Memory) for changing the symbol display mode of each display window. A plurality of display operation modes for each display window can be provided, such as stop mode, acceleration mode, constant speed rotation mode, and deceleration mode. Symbol data in each mode is transmitted to the display section 110 in frame span units. The ROM may be formed detachably or may use an ultraviolet ray erasable programmable read-only memory (EPROM) or an electrically erasable programmable read-only memory (EEPROM). The display control unit 401 stores image information output from the image processing unit 420 in a RAM and switches read of the symbol patterns stored in the ROM and the image information stored in the RAM at a specific time. For example, the image information stored in the RAM is read instead of reading a specific symbol from the ROM, whereby the image information input through the CCD camera section 121 can be displayed instead of displaying the specific symbol. The switching time and the switching method will be discussed later. The display section 110 displays a background picture stored in the VRAM and a symbol pattern in each display mode, in an overlapped manner. The display control unit 401 may display the image information stored in the RAM on the display section 110 or the second display section 110A as it is. For example, when an image is input, the input image may be displayed on the display section 110 enabling the player to check it. When the adjustment switch 107 is pressed, image information input and stored in the RAM may be erased. Further, the gaming machine may further include a write section for writing image information onto storage media, and an issuance section for issuing storage media on which image information is written. In this case, when the adjustment switch 107 is pressed, image information input and stored in the RAM may be written onto a storage medium, then the storage medium may be issued.

Next, the image input time and the image input method will be discussed.

The image input time is when a specific condition is satisfied. The specific condition is predefined in the game; control unit 403 or the image processing unit 420. The embodiment assumes that an image is input when a player continues to play games for a given time at the slot machine. Since players often change gaming machines for a short time, image input is enabled only for the player who continues to play games for the given time and can be suppressed for a player who changes gaming machines after a short time.

The game control unit 403, which can detect a player playing a game or not playing a game, detects that a game play has continued for a specific time after the transition is made from the non-gaming state to the gaming state. For example, the game control unit 403 can detect it by monitoring game play media used for the gaming. In this case, the specific time is set to, for example, one minute and if game play is continued for one minute, the game control unit 403 instructs the CCD camera section 121 to input an image through the image processing unit 420. The game play media used for gaming, or the number of game times, is counted, and when the value counted during the specific time from the non-gaming state reaches a predetermined value, the game control unit 403 may instruct the CCD camera section 121 to input an image. In this case, if the count does not reach the predetermined value during the specific time, image input is suppressed.

Then, the game control unit 403 sets a non-gaming state after a lapse of a specific time after the game is over, and further instructs the image processing unit 420 to erase the input image.

When the CCD camera section 121 is instructed to input an image, it starts shooting. After shooting, the CCD camera section 121 sends the image information to the image processing unit 420. For a color image, R, G, B signals, a luminance signal, and a synchronizing signal are sent for one frame, as the image information. For the television camera, an NTSC (National Television System Committee) signal is output.

Before shooting, the game control unit 403 may inform the player that he or she will be shot by outputting a predetermined message by voice through the loudspeaker 405 or displaying the message on the display section 110. Further, a cancel button 123 can be provided, as shown in FIG. 1, as inhibition specification means for accepting an inhibition instruction to the effect that an image is inhibited from being input during a specific time after the informing. When the player does not press the cancel button 123 during the specific time after the informing, an image is input; when the player presses the cancel button 123, image input is suppressed.

Another specific condition for the image input time may be predefined as follows:

For example, an image input specification button 122 of specification means for enabling image information to be input may be provided on the front of the gaming machine and when the button 122 is pressed, an image may be input. In this case, the player may press the image input specification button 122 only when he or she wants to display his or her appearances in place of a specific symbol. The image input specification button 122 is connected to the interface board unit 404 shown in FIG. 4 and when the button is pressed, a signal is sent to the game control unit 403. When receiving the signal from the image input specification button 122, the game control unit 403 instructs the CCD camera section 121 to input an image through the image processing unit 420.

Figure 8:
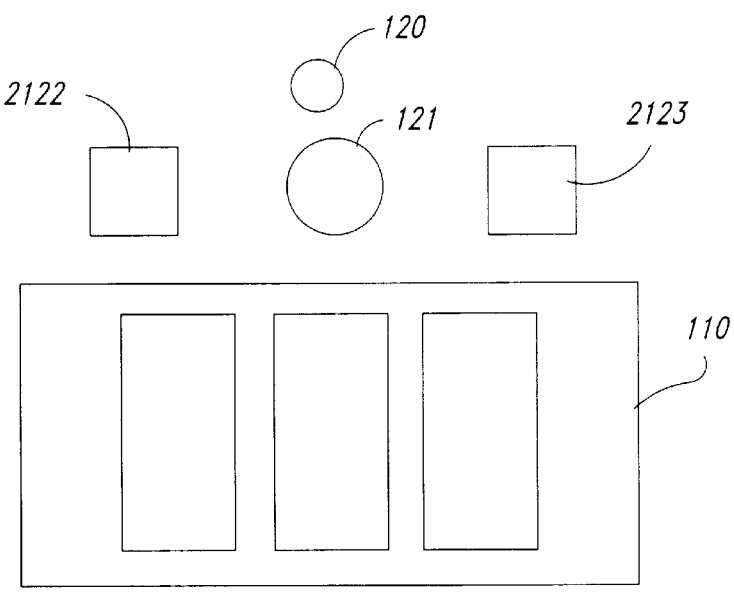
FIG. 8 is another front view of the slot machine in the embodiment.

Another specific condition for the image input time may be defined as a condition such that when a player faces the gaming machine for a given time, an image is to be input. In this case, a radiation section 2122 for radiating a signal of laser, infrared rays, etc., in a specific direction and a light receiving section 2123, such as a photo detector for receiving reflection of the signal from the specific direction, may be provided in front of the gaming machine, as shown in FIG. 8, and the specific condition may be defined as the time at which infrared rays have been received by the light receiving section 2123 for a specific time. In this case, the radiation section 2122 can comprise a laser diode or infrared light emitting diode for always radiating infrared rays toward the position where a player is assumed to exist when he or she plays a game, and when the light receiving section 2123 has received infrared rays for the specific time, the player can be detected as existing at the position. For example, when a seat or the like is placed in front of the gaming machine, the radiation section 2122 may be located on the seat and the light receiving section 2123 may be located in an opposed position rather than them being disposed in front of the gaming machine. In this case, when a player does not exist, light is received and when a player exists, light is not received. Therefore, when no light is received for a specific time, a player can be determined to exist. The radiation section 2122 and the light receiving section 2123 are connected to the interface board unit 404 shown in FIG. 4 and can be controlled by the game control unit 403.

Thus, image information can be input at the specific time.

Next, image processing will be discussed with reference to FIG. 3, which is a block diagram of the image processing unit.

Figure 3:
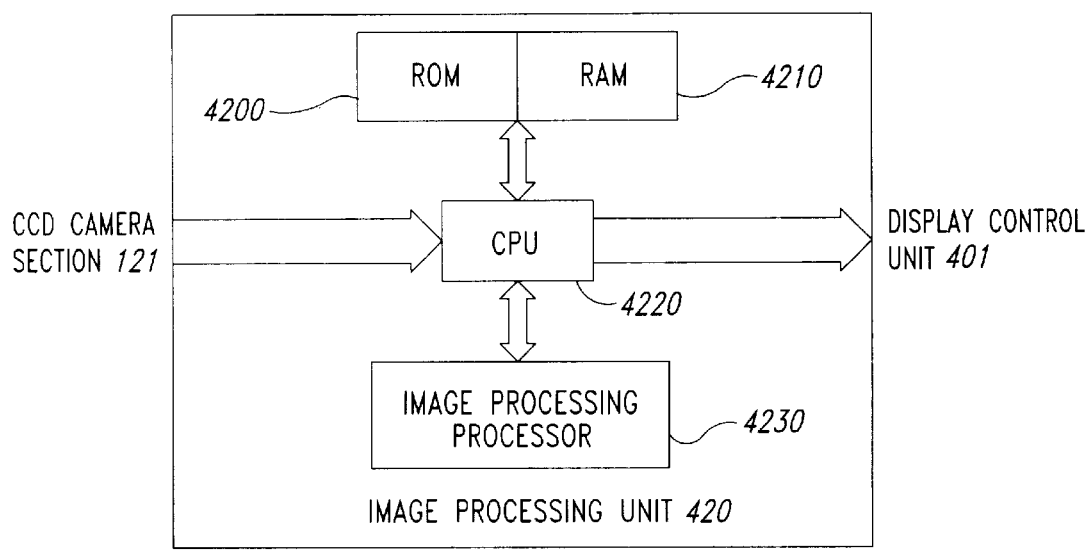
FIG. 3 is a block diagram of an image processing unit in the embodiment.

In FIG. 3, the image processing unit 420 comprises an image processing processor 4230, a ROM (read only memory) 4200 of an auxiliary storage for storing image processing programs, a RAM (random access memory) 4210 for accumulating image information, and a CPU 4220 of a control section. A digital signal processor (DSP) can be used as the image processing processor 4230.

When image information is output from the CCD camera section 121, the CPU 4220 sends an address and a write instruction to the RAM 4210 for storing the image information. For example, a player's face, etc., can be input as the image information. Next, the image processing processor 4230 is started for performing image processing. It enlarges, reduces, or compresses the image information output from the CCD camera section 121 so as to put the image information in one frame in the display control unit 401 for the display control unit 401 to display the image information on the display section 110. The image information output from the CCD camera section 121 maybe trimmed. That is, the image processing processor 4230 can perform at least one of an enlargement process for enlarging the read image information to a specific size, a reduction process for reducing the read image information to a specific size, a compression process for compressing the read image information to a specific size, and a trimming process for trimming the read image information to a specific size, as the image processing. In the embodiment, since the image information input through the CCD camera section 121 is displayed in place of a specific symbol, the image information is reduced so as to become equal to the information size of symbol information stored in the ROM contained in the display control unit 401. To display the image information input from the CCD camera section 121 on the entire display section, it is compressed to 1-frame image information in the display section 110. Further, the image processing processor 4230 may perform image processing such as smoothing, noise removal, and deletion of a background other than the player's face. It stores the image information in the RAM 4210 after processing, or may store read image information in the RAM 4210 as image information intact before image processing. After the termination of the image processing, the CPU 4220 sends the processed image information to the display control unit 401. If the size of image information input through the CCD camera section 121 is equal to the image information size that can be handled by the display control unit 401, the image processing may be skipped. By thus performing processing, the image information input through the CCD camera section 121 can be sent to the display control unit 401.

If the print section 421 is connected to the image processing unit 420 as shown in FIG. 4, after image processing is performed for read image information, the image information read from the print section 421 may be printed out. In this case, the image processing unit 420 causes the print section 421 to make a hard copy. To make a player check read image information, it may be output on the display section 110 or the second display section 110A.

Next, the configuration of the display control unit 401 will be discussed with reference to FIG. 5, which is a block diagram of the display control unit. The display control unit 401 comprises a VRAM for storing background pictures for switching screens at high speed, a display data ROM 1010 for storing display data of symbol portions of the slot machine, an image data RAM 1150 for storing image information output from the image processing unit 420, and an address generation section for outputting in sequence, for each frame, the display data ROM 1010 addresses of the symbols to be displayed in one frame in order for each frame to read out symbols or images from the display data ROM 1010 and the image data RAM 1150.

Figure 5:
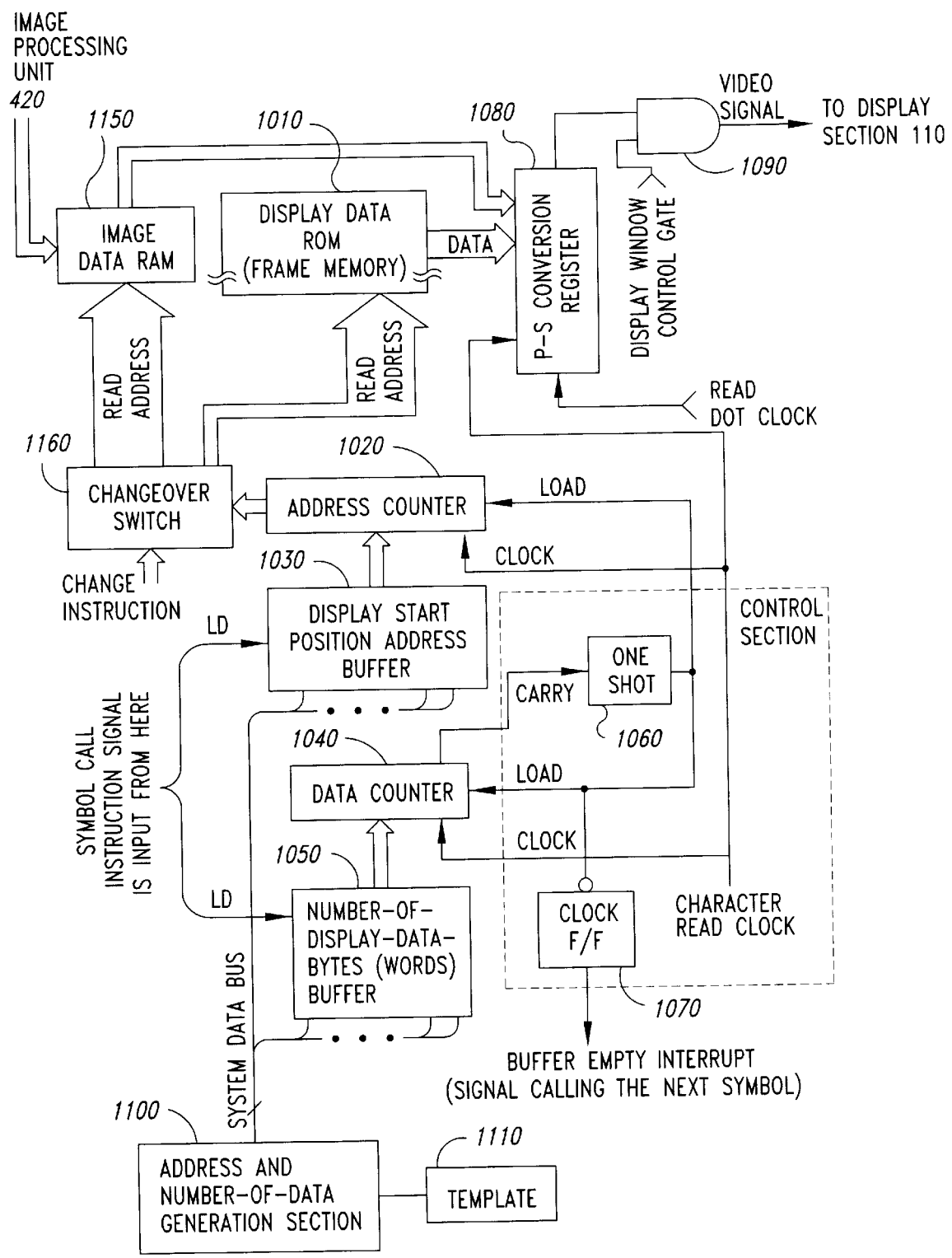
FIG. 5 is a block diagram of a display control unit in the embodiment.

In the embodiment, the configuration of display control for one display window in the display control unit 401 is as shown in FIG. 5, and to perform display control of three display windows, display control of each display window can be switched in a time-division manner. Assume that display on the display section 110 is performed for each row of each display window and that a predetermined area is displayed as the display area of each row, wherein about four symbols can be displayed at the same time, for example. The display section 110 updates display for a frame span of a given period every $\frac{1}{60}$ or $\frac{1}{30}$ seconds (V-sync period) and executes line scanning for each frame. The display control unit 401 reads symbols displayed in the display area of each row and displays the same symbols in the stop mode. During the rotation operation, it moves the display positions of the symbols displayed in the display area of each row. That is, when reading symbols from the ROM, the display control unit 401 shifts the read top position by a movement distance for each frame for reading the symbols displayed in the range of the display area and reads the symbols in a predetermined order, thereby displaying the symbols as if they had rotated. Further, in the embodiment, the movement distance is varied depending on the acceleration mode, constant speed mode, or deceleration mode. In the acceleration mode, a change is made from a still picture pattern read to a flow-condition pattern read.

The address generation section comprises: 2) an address counter 1020, 3) a display start position address buffer 1030, 4) a data counter 1040, 5) a number-of-display-data-bytes (words) buffer 1050, 6) an address and number-of-data generation section 1100, and 7) a change-over switch 1160.

Figure 10:
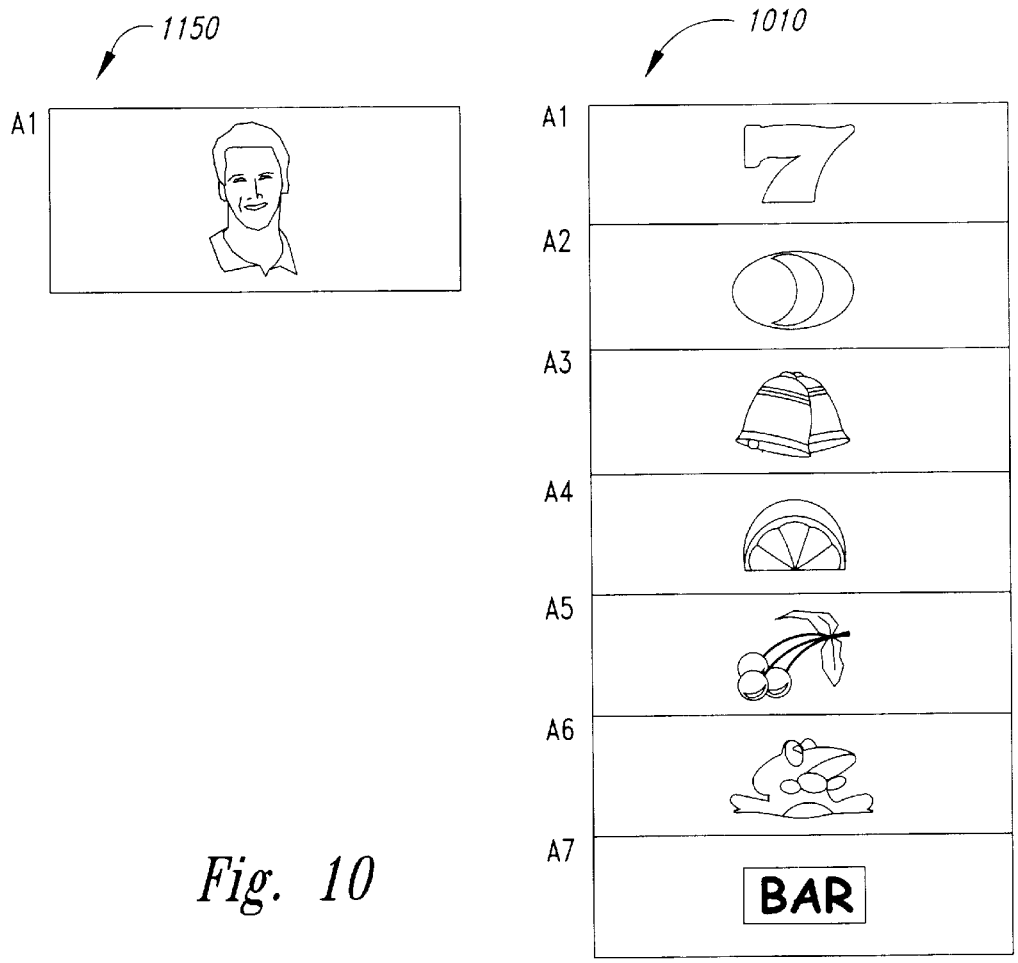
FIG. 10 is an illustration showing the storage contents in memories in the embodiment.

1) All symbol data to be displayed is stored in the display data ROM 1010. In this case, the display data ROM 1010 may store the symbol data patterns to be displayed for each display window or one display data ROM 1010 may be provided for all display windows. For example, a plurality of data patterns are stored in the display data ROM 1010 as shown in FIG. 10. Image information sent out from the image processing unit 420 is stored in a predetermined address of the image data RAM 1150 as shown in FIG. 10. To display the image information sent out from the image processing unit 420 in place of a specific symbol, the image information is stored in the image data RAM 1150 area having the same address as the address of the specific symbol pattern stored in the display data ROM 1010. The image data RAM 1150 is provided only with the area for storing the image information sent out from the image processing unit 420 (corresponding to the data capacity of one symbol pattern).

2) The address counter 1020 is a counter for reading out the contents of the display data ROM 1010. The read start address is loaded into the ddress counter 1020, which then counts up (or down) in sequence in response to character read clock.

3) The display start position address buffer 1030 is a buffer for toring the read start address of the next symbol to be displayed. Upon ompletion of displaying the preceding symbol, data is loaded into the address counter. The read start address is generated by the address and number-of-data generation section 1100 described below, and is sent out on a system data bus.

4) The data counter 1040 is a counter for checking how many bytes (or words) of a display pattern are to be displayed. The number of data bytes (words) in the number-of-display-data-bytes (words) buffer is loaded into the data counter 1040, which then counts down in response to a character read clock. When the number reaches 0, a carry signal is output, a load signal is output from a one-shot circuit 1060, and new data is loaded.

5) The number-of-display-data-bytes (words) buffer 1050 is a buffer for storing data defining the number of bytes (or words) of the next symbol to be displayed. When the data counter reaches 0, the number is read into the data counter.

6) The address and number-of-data generation section 1100 generates the read start address and the number of bytes of the symbol to be displayed. Thus, it comprises a template 1110 provided for each frame for storing at least the read start position of the symbol displayed at the top stage of the display section in one frame, the read data amount, and a flag indicating whether or not a new symbol pattern is to be displayed.

7) The change-over switch 1160 is a switch of change-over means for changing information read from the display data ROM 1010 and information read from the image data RAM 1150. A change instruction is given by the game control unit 403 as described below. For the address of a specific symbol specified from the address counter, the memory to be accessed is changed by the change-over switch 1160 in response to the change instruction.

FIG. 6 is an illustration showing the template. As shown here, the template 1110 can comprise, for example, a stop mode showing a display stop state, an acceleration mode showing a rotating display state with acceleration, a constant speed rotation operation mode showing a rotating display state at a constant speed, and a decelerating mode showing a rotating display state with deceleration. In the stop mode, symbols do not move and the same symbol is updated every frame. As described below, when an operation start signal is accepted from a microprocessor 408, each display window makes the transition to the acceleration mode and the speed is accelerated until a predetermined symbol movement speed is reached. When the predetermined symbol movement speed is reached (or a given time has elapsed), the transition is made to the constant speed mode. When an operation stop signal is accepted from the microprocessor 408, the operation is decelerated at a predetermined deceleration speed. When a predetermined symbol movement speed is reached (or a given time has elapsed), the stop mode is entered.

A data configuration example of a template table is shown in FIG. 6 (iv), wherein (a) denotes the read start position of the symbol displayed at the top stage of the display section in the display data ROM 1010 storing the displayed symbol. The read start position (a) indicates a bias value; when the start position for each symbol pattern stored in the display data ROM 1010 is assumed to be 0, the number of rasters from the start position to the read start position (number of rasters=total number of bytes of one symbol/16) is indicated. This makes it possible to determine at what position of the symbol display is to be started. Further, (b) denotes the number of display data bytes read in one frame.

Thus, the template stores the read start position and the number of data bytes for each frame. Symbols can be displayed as if they had rotated by shifting the read start position little by little for each template. The shift amount corresponds to the movement distance of the symbol display position for each frame. The rotation speed can be varied from one display section to another by providing the template for each display section.

Figure 7:
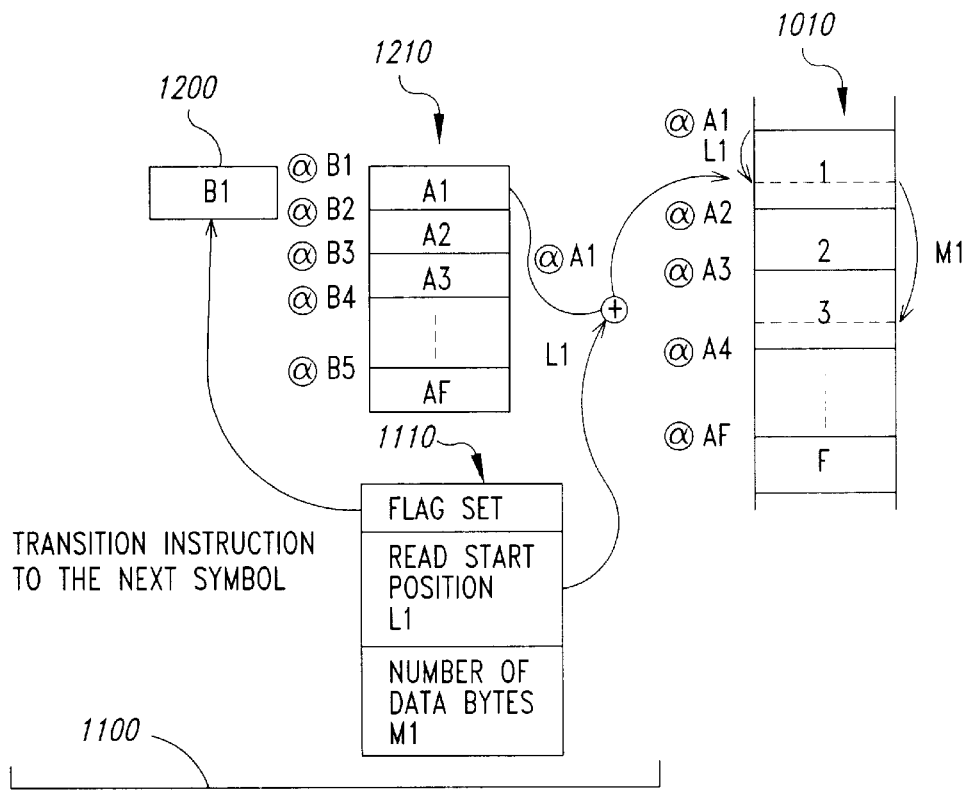
FIG. 7 is an illustration of the address generation operation in the embodiment.
Figure 9:
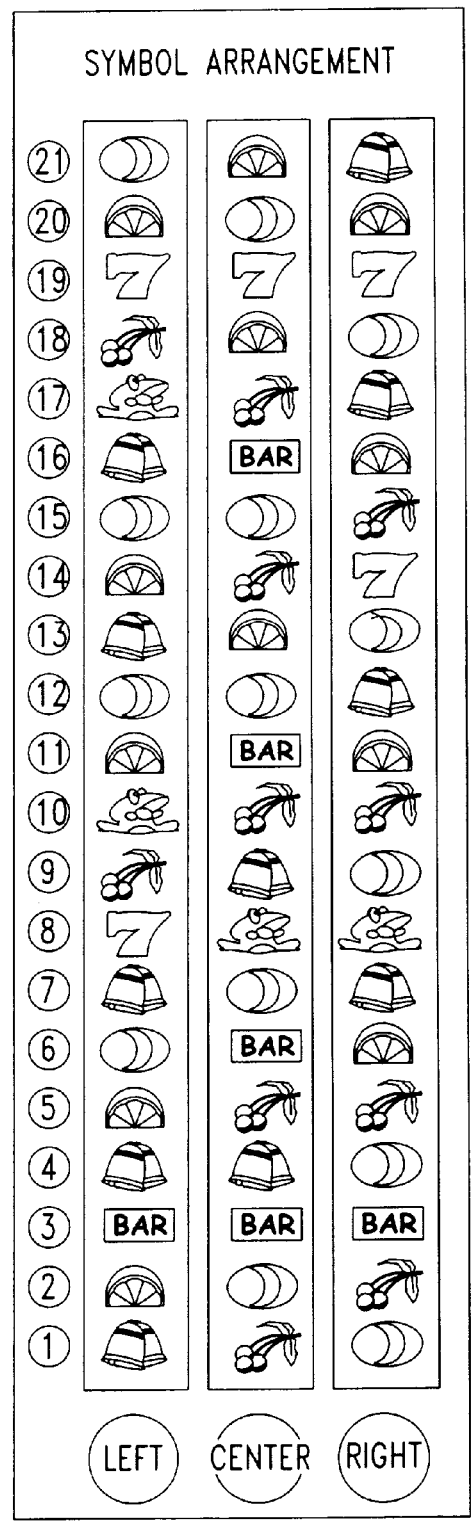
FIG. 9 is an illustration showing an example of symbol arrangement in the embodiment.

The address and number-of-data generation section 1100 further includes, as shown in FIG. 7, a symbol register 1210 for storing the start address for each symbol pattern and a symbol pointer 1200 serving as a pointer to the symbol register 1210. The symbol pointer 1200 points to the symbol at the top stage on each display window and is incremented according to the template contents. That is, when the flag indicates display of a new symbol pattern, the symbol pointer 1200 is updated so as to point to the next symbol. The symbol register 1210 holds the symbol pattern start address for each display order. For example, if the display order is defined to display in the symbol arrangement as shown in FIG. 9, the address for each symbol stored in the display data ROM 1010 is stored in the symbol register 1210 in relation to the symbol arrangement order.

As shown in FIG. 7, the address and number-of-data generation section 1100 reads the start address of the symbol pattern stored in the symbol register 1210 pointed to by the symbol pointer 1200 for each frame, looks up in the symbol template 1110, and adds the read start position and the symbol pattern start address, thereby generating the read start address. The number of bytes of the symbol to be displayed is the read data amount in the symbol template 1110.

Next, a template processing procedure will be discussed with reference to FIG. 6, wherein a move pointer is provided to point to the template table position. The move pointer can be made of a counter for indicating the display template read position. It counts up in sequence with the display timing as a clock and when counting up to the last template, it returns to 0. The data read from the template table is temporarily accumulated in a temporary work area.

(1) After the power of the pachinko machine is turned on or when an instruction is received from the microprocessor, the display control unit 401 repeats reading of template SSDT0 (stop mode).

(2) Upon acceptance of an operation start signal from the microprocessor, the template is set to SSDT1, template SSDT1 data is expanded, and the data expanded for the next frame is written into the temporary area.

(3) Each time the frame is updated (namely, each time the display timing arrives), the template is set to SSDT2, SSDT3, . . . , and this sequence is repeated.

(4) Upon completion of the acceleration template process, the transition is made to the constant speed template process and this process is repeated in a similar manner (a loop of CNDT14 to CNDT0 is repeated).

Next, the display operation in FIG. 5 will be discussed.

1. The address and number-of-data generation section 1100 refers to the template as described above, generates the <read start address> and <number of display data bytes> of the symbol to be displayed as a 1-frame table, stores the read start address in the display start position address buffer 1030, and stores the number of display data bytes in the number-of-display-data-bytes buffer.

2. The read start address and the number of display data bytes are loaded into the address counter and the data counter conforming to the display timing.

3. In the current frame, the address and number-of-data-bytes generation section creates a table of data to be displayed in the next frame.

4. The data counter 1040 and the address counter 1020 operate according to clocks and data is read from the memory according to the address indicated by the address counter 1020.

5. The change-over switch 1160 operates so that data is normally read from the display data ROM 1010 and that to display image information output from the image processing unit 420 in place of a specific symbol, data is read from the image data RAM 1150.

Thus, the address generation section generates addresses, symbol data is read from the display data ROM 1010, and image information can be read from the image data RAM 1150 instead of a specific symbol.

As another configuration, the start address stored in the symbol register 1210 shown in FIG. 7 may be rewritten without providing the change-over switch 1160. In this case, the address assigned to the display data ROM 1010 and the address assigned to the image data RAM 1150 are made separate to prevent them from overlapping each other. For example, start address "A1" stored in the symbol register 1210 is held in another register provided and instead the start address of the image data RAM 1150 is held in the symbol register 1210. To restore to the former specific symbol, the held start address "A1" may be restored to the symbol register 1210. In this case, the address line from the address counter 1020 is connected to both the image data RAM 1150 and the display data ROM 1010. The image information input instead of a specific symbol can also be displayed in such a manner.

Next, the change time for displaying the image information output from the image processing unit 420 instead of a specific symbol will be discussed. The change time is the change timing specified for the change-over switch; in the embodiment, it is specified by the game control unit 403, but another control section may be provided for the purpose.

To specify the change time, change detection means for detecting a specific condition being satisfied is provided and when the change detection means detects it, a change is made so as to display the image information output from the image processing unit 420 instead of a specific symbol.

The following conditions may be predefined as the specific condition:

A first specific condition is satisfied when data is stored in the image data RAM 1150 after image processing by the image processing unit 420. In this case, the change detection means detects data being stored in the image data RAM 1150, then outputs a change instruction so as to display the image information output from the image processing unit 420 instead of a specific symbol. When the change instruction is output, for example, if instead of a specific symbol, such as the symbol "7" with the address A1 as the start address shown in FIG. 10, the address corresponding to the symbol "7" is specified, the change-over switch 1160 instructs data to be read from the image data RAM 1150. By predefining the condition, after an image is input, a change can be made to the image information provided by inputting a specific picture just after image processing.

A second specific condition is as follows: An image change specification button 124 of specification means for specifying permission of changing the image information is further provided. The change detection means detects the time at which a permission instruction is given through the specification means. For example, after an image is input and the input image information is output from the print section 421, a player checks the image information as described above, then presses the image change specification button 124. In response to this, a change is made so as to display the image information output from the image processing unit 420 instead of a specific symbol, whereby the player can display the input image information whenever he or she wants it; the player can be much more conscious of taking part in a game and can enjoy playing the game.

A third specific condition is as follows: A plurality of types of symbols are displayed and controlled at a plurality of positions as image information. The game control unit 403 comprises determination means for determining whether or not a combination of the symbols displayed at the positions is a predetermined symbol combination. The change detection means detects the specific condition when the determination means determines that the combination of the symbols displayed at the positions is the predetermined symbol combination. For example, when three display windows exist, if as a predetermined symbol combination, the symbols displayed at the centers of the display windows are the same, a change can be made so as to read data from the image data RAM 1150. The same change may be made, when two of the three display windows are stopped and symbols are displayed only on one display window, if the same symbol as the symbol displayed at the center of each stopped display window is displayed on the operating display window as a predetermined symbol combination, a change may be made so as to read data from the image data RAM 1150. In doing so, when the symbols match a specific combination, a change can be made to the input image information, so that the player can enjoy playing a game much more.

By thus predefining the change conditions, a change can be made if the defined condition is satisfied.

Figure 11:
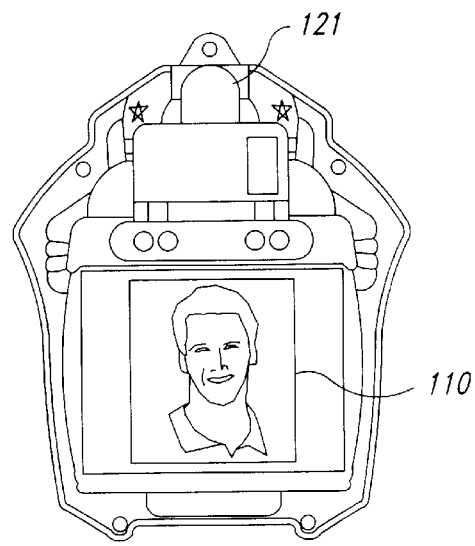
FIG. 11 is another front view of the slot machine in the embodiment.

Although the image information input instead of a specific symbol is displayed in the embodiment, image information input instead of any other display information may be displayed. For example, as shown in FIG. 11, input image information may be displayed on the entire display section 110 instead of display window and symbol display. The front view shown in FIG. 11 provided by extracting the display portion of a pachinko machine, etc., and its peripheral portion.

Figure 12A:
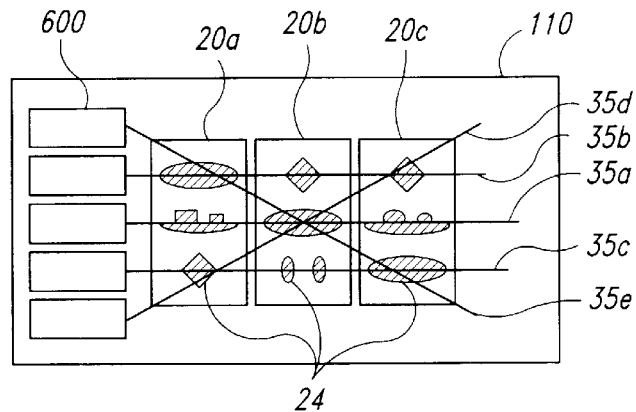
FIG. 12 is a display illustration of a display section of the slot machine in the embodiment.
Figure 12B:
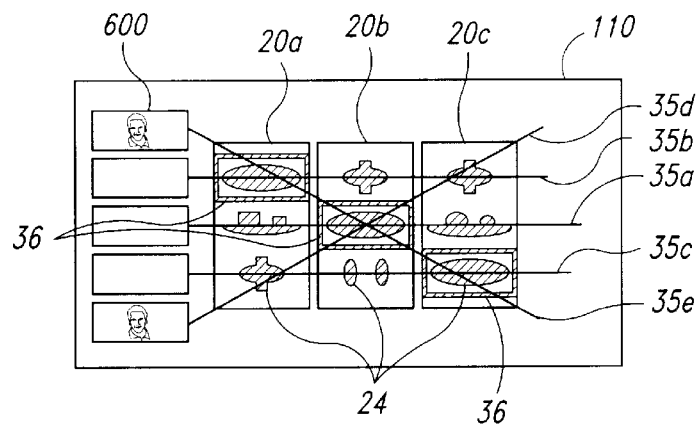

If a plurality of gaming lines (betting lines) each having a combination of symbols at a plurality of positions are defined in the game control unit 403 and at least one or more of the gaming lines are selected and the display control unit 401 is instructed to indicate selection of the gaming line, the display control unit 401 may control so as to display the symbols at the positions and indicate selection of the gaming line by using input image information. For example, as shown in FIG. 12, the gaming lines are defined as 35a, 35b, 35c, 35d, and 35e. To indicate gaming line selection when a player selects one or more of the gaming lines or one or more of the gaming lines are selected in response to the number of input game play media, the display section 110 may be provided with an area 600 for each gaming line and the input image information may be displayed in the areas 600 corresponding to the selected gaming lines. If the gaming lines are selected, the input image information can be displayed in the areas 600 as shown in FIG. 12(B).

Next, the hardware configuration for displaying input image information as described above will be discussed with reference to FIG. 14, which is a block diagram of the hardware for displaying an input image as a background.

Figure 14:
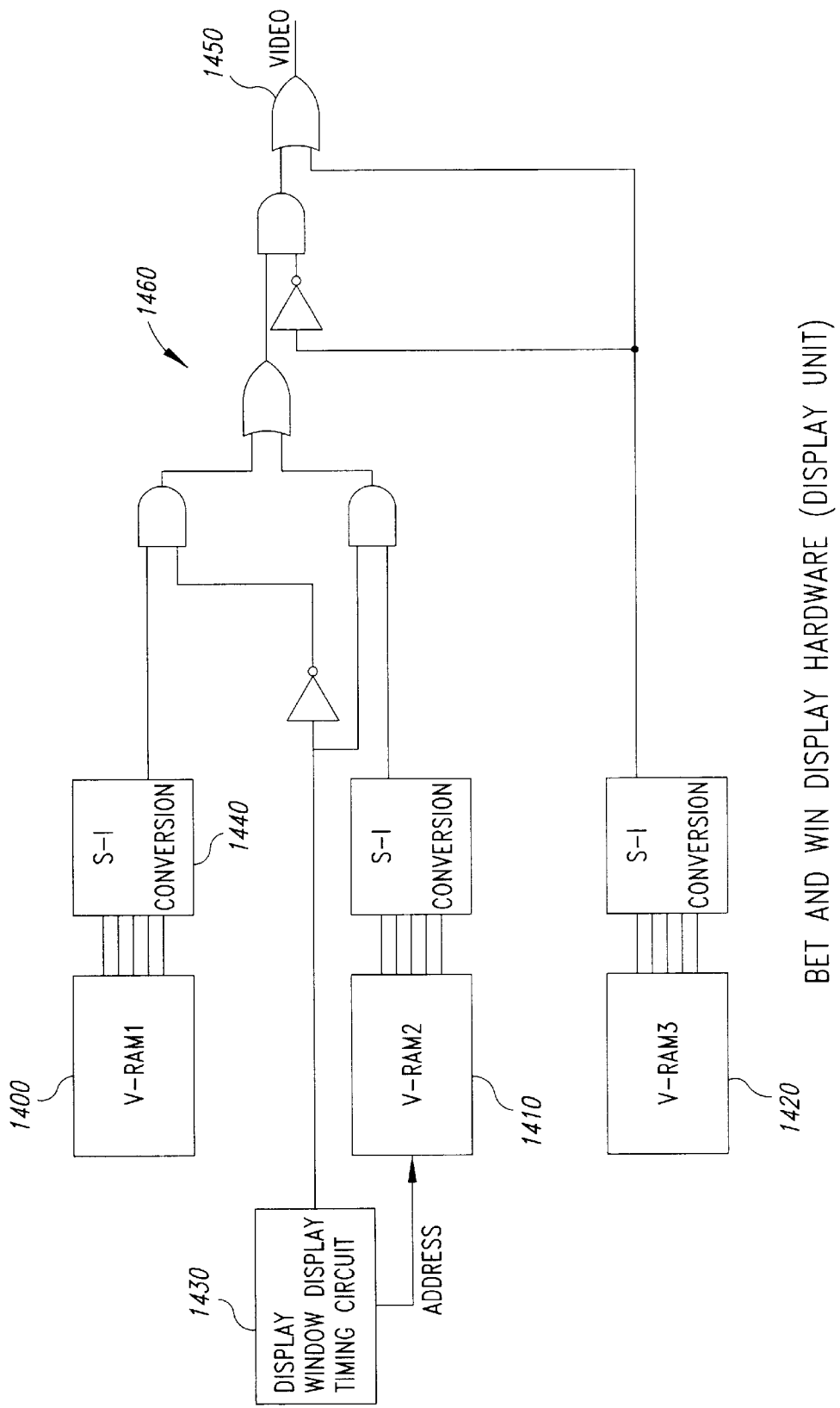
FIG. 14 is a block diagram of a display control unit in the embodiment.

Images other than symbol display in display window portions, such as the gaming lines as shown in FIG. 12, are stored in V-RAM 1420 or V-RAM 1400 of background storage means shown in FIG. 14 as background pictures. Additional one or more V-RAMs of background storage means may be provided. In the embodiment, a plurality of different backgrounds are provided. In this case, a respective the V-RAM is provided for each background or one V-RAM is divided into regions for use. In FIG. 14, the V-RAM 1420 is provided for the betting lines indicating selected gaming lines. It is win combination storage means for the betting lines and win display, and previously stores the betting lines and win display corresponding to the bet rates. The V-RAM 1400 stores background data other than the betting lines or win display; input image information may be stored in the V-RAM 1400 for indicating selection of gaming lines. V-RAM 1410 is symbol storage means for storing display window symbols, and maybe made of a ROM as described above. The symbol storage means, the background storage means, and the win combination storage means are controlled in output by display control means.

To display input image information on the entire display section 110 instead of display window and symbol display as shown in FIG. 11 as discussed above, or to indicate the gaming lines and selection thereof as shown in FIG. 12, the image information output from the image processing unit 420 shown in FIG. 3 is stored in a predetermined area of the V-RAM 1400. The data stored in the V-RAM 1420 has all frame data displayed on the display screen and the betting lines and win display are stored as high data and others as low data. A gate circuit 1460 allows output from other V-RAMs to take precedence over the low data portion, whereby video signals output from the V-RAMs can be changed by the data itself stored in the V-RAM 1420. In the circuitry shown in FIG. 14, the data stored in the V-RAM 1420 is displayed taking precedence over any other data. The V-RAM 1400 stores background data and read of the V-RAM 1400 and V-RAM 1410 is controlled by a display window display timing circuit 1430.

In FIG. 14, the symbol data stored in the V-RAM 1410 is read taking precedence over the background data in the V-RAM 1400 as instructed by the display window display timing circuit 1430 of the display control means. The V-RAM 1410 is read when an address is specified by the display control unit; when the address is specified, the V-RAM 1410 is read taking precedence over the V-RAM 1400 and when no address is specified, data in the V-RAM 1400 is read. The V-RAM 1400 is read out, whenever necessary, as instructed from a sequential counter (not shown). The top addresses are prestored in a betting line table corresponding to the identification numbers of the betting lines and win display responsive to the bet rates. To read the V-RAM 1420, the game control unit specifies the betting line table based on the betting line identification number so as to indicate the betting line or win display, and the top address corresponding to the identification number is read. Predetermined V-RAM 1420 area is read starting at the top address and the corresponding betting line or win display is displayed. Likewise, input image information is read from the V-RAM 1400 in response to the selected gaming line. Thus, when one or more gaming lines are selected, the input image information can be displayed in the areas 600 as shown in FIG. 12(B).

To display input image information on the entire display section 110 instead of display window and symbol display as shown in FIG. 11, 1-frame image information is prestored in a predetermined area of the V-RAM 1400 from the image processing unit 420 and can be read at a specific time for displaying the input image information on the entire display section 110.

The input image information may also be displayed in a specific area of a background other than symbol display.

Figure 13:
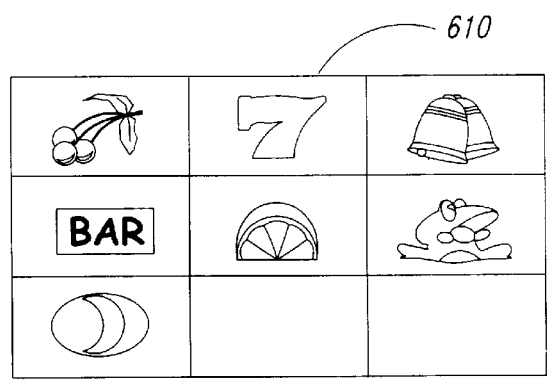
FIG. 13 is an illustration showing a display example of a symbol specification section in the embodiment.

Further, a player may specify the image information to be changed. For example, the background may be divided into regions and region specification means or the like may be provided for each region for the player to specify the region in which the input image information is to be displayed, whereby the input image information can be displayed in the specified region. The player may also be able to specify a specific symbol. In this case, for example, a plurality of types of symbols are displayed and specification of any symbol can be accepted. A symbol specification section 610 as shown in FIG. 13 may be provided on the front of the gaming machine for allowing a player to specify one of the symbols for displaying input image information instead of the specified symbol. This enables the player to select the symbol to be changed and to enjoy playing a game much more.

A plurality of image information icons to be used for replacement may be defined. For example, a plurality of different image information icons are input through the camera section 121 and may be displayed for selection in a second display section having an appearance as shown in FIG. 13 for displaying nine icons of image information. Further, the second display section is provided with an input image selection section for accepting selection of read of any of the image information icons from the outside, whereby the player can select his or her favorite image information and enjoy playing a game much more.

Further, the image processing unit may convert the image information accepted through the image input section into image information of different specific sizes. More than one specific condition for the image change is defined and one of the image information icons of specific sizes is defined as read image information for each specific condition defined.

Thus, by predefining a specific condition for input, when the specific condition is satisfied, input image information can be displayed instead of specific image information.

Figure 2:
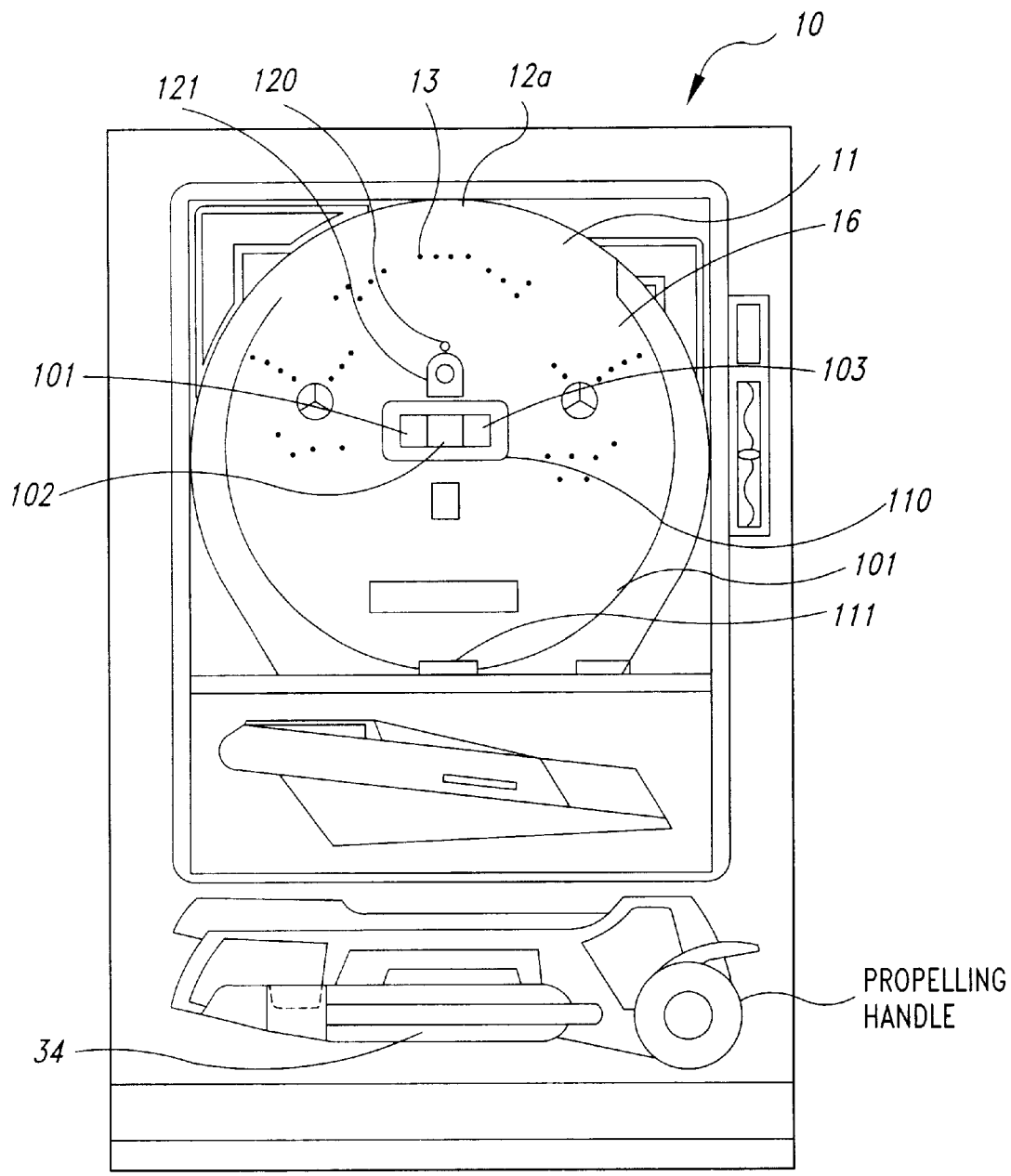
FIG. 2 is a front view of a pachinko machine in the embodiment.

Although we have discussed the invention for the slot machine in the embodiment, it may be applied to a pachinko machine as shown in FIG. 2, which is an external view of the pachinko machine. In FIG. 2, a display section 110 such as a CRT or liquid crystal display, a CCD (Charge Coupled Device) camera section 121 of means for picking up an image of an object, and illumination means 120, such as a flash connected to the CCD camera section 121 for illuminating an object, are placed on a game board 101. The hardware configuration can be similar to that of the slot machine discussed above, and game progress control conforming to pachinko games may be performed by a game control unit 403.

Next, an embodiment wherein an image input system is not integral with a gaming machine will be discussed with reference to FIG. 15, which is a block diagram of the image input system. In the embodiment, an image input through the CCD camera section 121 is processed and stored on a storage medium, which is then mounted on the gaming machine for reading the image information, whereby the image information stored on the storage medium is displayed instead of a specific symbol as described above. In this case, the image input system is located at the doorway, etc., of the gaming house and can be used by a player only when he or she wants to use it. The image input system need not be provided for each gaming machine.

Figure 15:
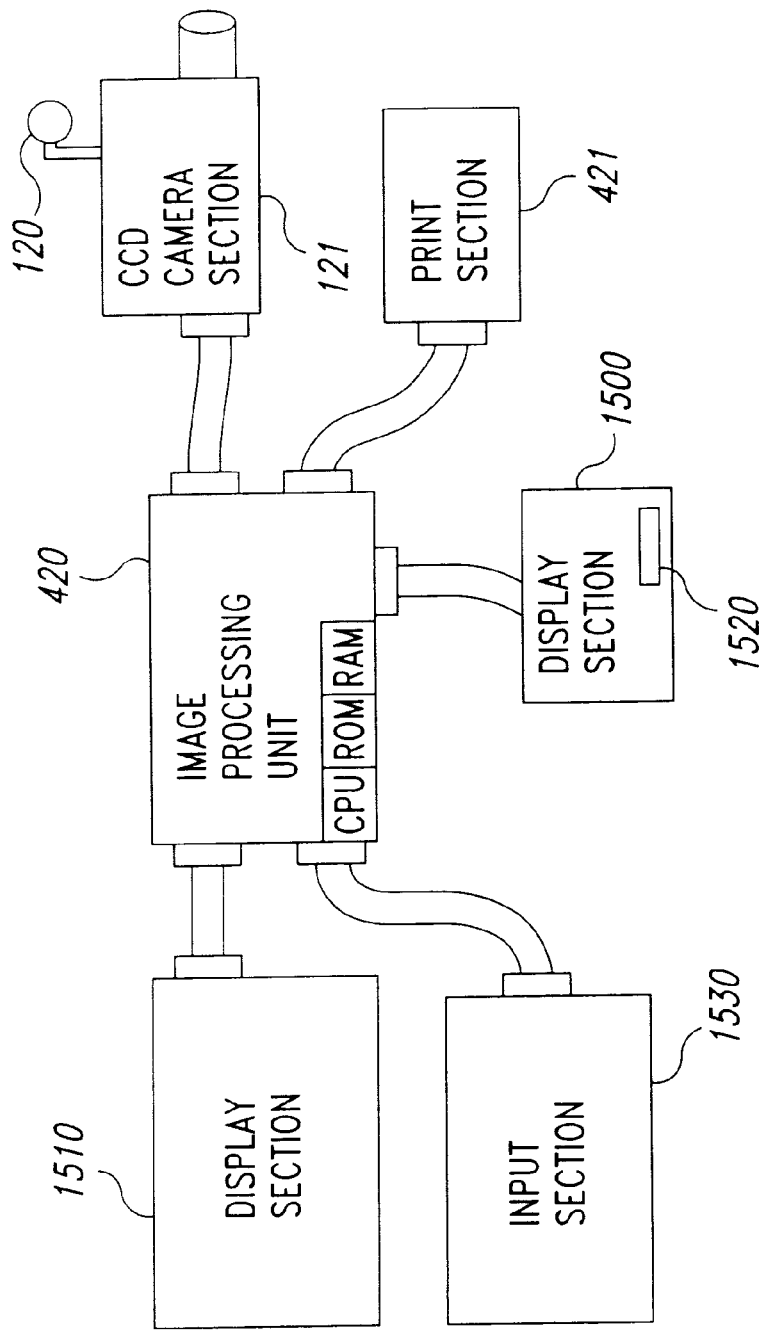
FIG. 15 is a block diagram of an image input system in another embodiment.

In FIG. 15, the image input system comprises a CCD (Charge Coupled Device) camera section 121 of image picking-up means, an image processing unit 420 for processing an image input through the CCD camera section 121 and outputting the image information to a display control unit 401, an image write section 1500 for storing input image information on a storage medium, a display section 1510 for monitoring the input image information, and an input section 1530 for accepting an instruction such as an image information taking-in instruction. It may further include a print section 421 such as a printer connected to the image processing unit 420 for printing out the input image information. The CCD camera section 121 may be provided with an automatic focusing function. The image input system may further include illumination means 120 such as a flash connected to the CCD camera section 121 for illuminating an object. It may comprise a card issuing unit for issuing cards.

The image write section 1500 comprises a card mounting section 1520 for mounting a storage medium such as an IC card and writes image information output from the image processing unit 420 into a predetermined area. It may further include a read section for reading information stored on the card.

The display section 1510, such as a CRT or liquid crystal display, displays input image information for a player to check it.

The input section 1530 accepts an image taking-in instruction, specification of a write area of a storage medium, an image size, etc., and sends them to the image processing unit 420. For the write area of a storage medium and the image size, image information for a specific area and a specific capacity may be predefined in the image processing unit 420. The input section 1530 may be provided with the cancel button 123, etc., disposed on the front of the slot machine described above.

Further, the card may be provided with a display section for displaying input image information as visible information. For example, a photo showing the appearance of the card holder is displayed on the display section of the card. The card may also serve as a card for storing credit information such as the number of game play media held so far, a gaming house membership card for storing information concerning the card holder, or the like. If the card also serves as the membership card, once image information is written onto the membership card, when the card holder returns to the gaming house, he or she may use the membership card for playing a game.

The CCD camera section 121 and the image processing unit 420 have the functions as described above.

In this case, the gaming house comprises an image information read section for reading cards. An input/output section 102b is provided as shown in FIG. 1, and an input/output section 102 is provided with a card reader/writer 311 as shown in FIG. 4 for reading/writing information from/onto a card inserted therein.

In FIG. 15, when an image taking-in instruction is accepted through the input section 1530, the CCD camera section 121 starts shooting. After shooting, the CCD camera section 121 sends image information to the image processing unit 420. Before shooting, the image processing unit 420 may inform the player that he or she will be shot by outputting a predetermined voice message through a loudspeaker provided, or by displaying the message on the display section 1510.

After shooting, the input image information is displayed on the display section 1510. After the player checks the image information on the display section 1510, the image processing unit 420 processes the input image information as described above, and after the image processing, the image information is stored in RAM. For example, the image processing unit 402 performs the image processing so as to output image information reduced for display, instead of a specific symbol and image information for display, on the entire display section 110 of the gaming machine.

Then, when an instruction for writing the information onto a storage medium is accepted through the input section 1530 or after the image processing is completed, the image processing unit 420 transfers the image information to the image write section 1500, which then writes the image information onto a card and outputs the card.

When playing a game, the player can mount the card on the card reader/writer 311 of the gaming machine for reading the image information. The image information read from the card is written into a specific area of the image data RAM 1150 or the V-RAM 1400 of the display control unit 401, and the display control unit 401 performs control as described above. The gaming machine may be provided with a taking-out button within the specification means, for accepting an instruction for taking out the card inserted in an insertion slot, for taking out the card when the game is over; upon acceptance of the instruction, the card may be output.

By performing the operation as described above, image information can be input and displayed instead of gaming image information. Once a card storing the image information is issued, if the player uses the card, the image information stored on the card can be displayed instead of symbols, without inputting the image information. To change the image information stored on the card, it may be rewritten.

As we have discussed, according to the embodiment, image information can be input and displayed instead of gaming image information, whereby the player can have a sense of taking part in a game and can enjoy playing a game. Therefore, the hall having the gaming machines of the invention can also expect an increase in the number of players.

Figure 16:
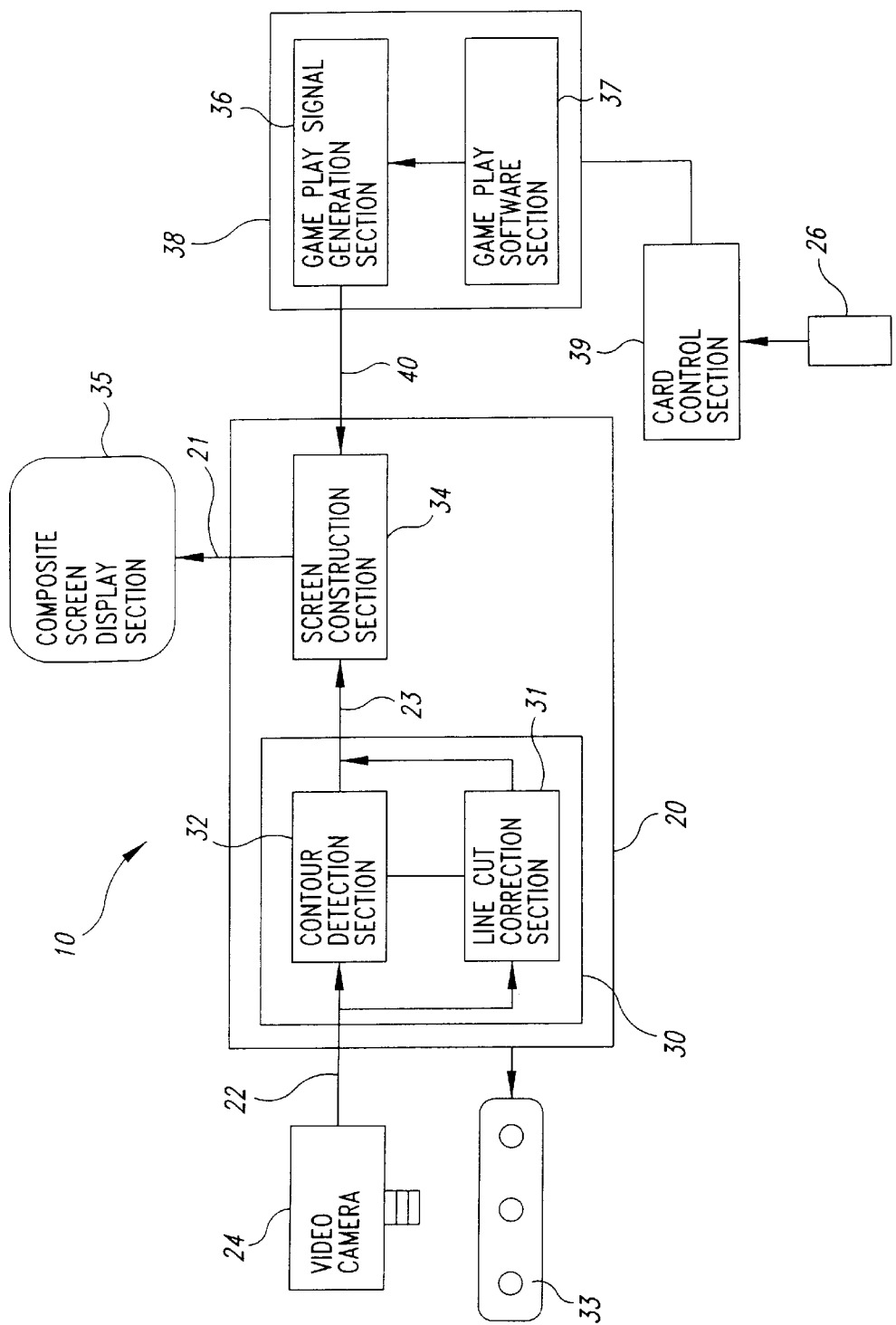
FIG. 16 is a block diagram of an image input gaming system in another embodiment.

Next, another embodiment of the invention will be discussed. FIG. 16 is a block diagram showing a gaming machine according to another embodiment. In the embodiment, input image information is displayed on a card as visible information.

As shown in FIG. 16, a gaming machine 10 changes displayed symbols in synchronization with game play for carrying out game play progress. The game play refers to symbol match game executed on a display screen of a slot machine, a pachinko slot (pachinko machine having a symbol display function similar to that of a slot machine), etc., a role playing game using characters appearing on a video game, or the like.

The gaming machine which changes displayed symbols for carrying out game play progress comprises a video camera 24 for inputting image data 22, a face position specification lamp display section 33 for specifying the direction in which the video camera 24 shoots a player, symbol change means 20 for generating symbol data 21 used for game play and changing symbols based on the symbol data 21, game play control means 38 for reading stored game play programs in sequence and outputting a game play control signal 40 for controlling the game play progress to the symbol change means 20, a composite screen display section 35 for receiving the symbol data 21 from the symbol change means 20 and displaying symbols used for game play, a recyclable card 26 from and onto which data can be read and written, and a card control section 39 for reading/writing data from/onto the recyclable card 26.

The video camera 24 and the face position specification lamp display section 33 for specifying the direction in which a player is shot are disposed near the gaming machine.

The video camera 24 can use CCDs or an image pickup tube (Chalnicon, vidicon, or the like). Either digital or analog signals can be used for video signals. An analog video camera 24 would be able to reduce machine costs. A digital video camera 24 would be able to provide a compact camera, enable high-speed data transmission, and facilitate brightness control and white balance adjustment, improving maintainability of the gaming machine.

Further, if a digital signal processor (DSP) is used to enhance the efficiency of image processing such as contour detection processing and line cut correction processing, use of digital signals as output of the video camera would improve the processing efficiency. In the embodiment, good image characteristics can be provided as a result of using a digital CCD video camera.

The symbol change means 20, which generates symbol data 21 used for game play and changes symbols based on the symbol data 21, comprises a line drawing creation section 30 for generating a line drawing as a reduced image 23 provided by reducing the data capacity of the image data 22 input through the video camera 24 and a screen construction section 34 for generating symbol data 21 based on the line drawing and outputting it to the composite screen display section 35.

In the embodiment, the symbol change means 20 is provided by an electronic circuit using a microprocessor. A digital signal i processor (DSP) and a flash memory are effective means for enhancing the efficiency of image processing such as contour detection processing and line cut correction processing.

Then, for example, facial expressions of a player, etc., input through the video camera 24 can be used as a symbol or facial expressions of a character, enabling the player to enjoy playing a game.

The line drawing creation section 30, which generates a line drawing as a reduced image 23, comprises a line cut correction section 31 for adjusting the image density and a contour detection section 32 for enhancing contour lines and generating a line drawing (reduced image 23) using image data resulting from the line cut correction.

The image construction section 34 receives a game play control signal 40 from the game play control means 38 and a reduced image 23 from the line drawing creation section 30, generates symbol data 21, and outputs it to the composite screen display section 35.

The game play control means 38 comprises a game play software section 37 for storing a control program of game play command input, screen display, voice output, etc., and a game play signal generation section 36 for reading the program for making game play progress.

In the embodiment, a microprocessor and RAM provide the functions of the line cut correction section 31 and the contour detection section 32. Image processing of line cut correction, contour detection, etc., is executed in software.

The recyclable card 26 has all or part colored in a color that stands out with respect to white and comprises on the colored surface a rewritable, recyclable display layer made of an organic compound which becomes cloudy with a crystal coagulating upon application of heat at one specific temperature and becomes transparent with the crystal diffusing upon application of heat at another given temperature.

The card control section 39 writes visually the reduced image 23 used for the game play onto the surface of the recyclable card 26 at a player's request or at game play adjustment in response to an instruction from the game play control means 38, etc., it is used in a state in which it is connected to the game play control means 38. The recyclable card 26 is inserted for use into a card slot (not shown) made in the card control section 39.

A back coating layer is laminated on the surface of a plastic card base forming the recyclable card 26. It may be formed of a colored film, an aluminum film, etc., in addition to pigments. Predetermined entries are made on the surface of the recyclable card 26 in thermally colored ink.

The thermally colored ink is used widely and generally for thermal copy paper, etc., and is made of a compound which is normally transparent and is heated to present a given color.

A recyclable display layer made of an organic compound which becomes cloudy with a crystal coagulating upon application of heat at one specific temperature and becomes transparent with the crystal diffusing upon application of heat at another given temperature is laminated on the surface of the back coating layer. For example, it comprises an organic compound of a higher fatty acid such as a behenic acid, a lauric acid, or a stearic acid dispersed in a polymeric matrix material of vinylidene chloride, etc., to which a small amount of a surface active agent, etc., is added.

When the recyclable display layer is heated at a specific temperature (100° C. or higher), namely, a write temperature, particles of the organic compound change to be polycrystalline, generating irregular reflection, thus making the layer cloudy and visible. On the other hand, when the layer is heated at another specific temperature (70–95° C.), namely, an erasion temperature, the crystal becomes monocrystalline and diffuses, thus making the layer transparent.

Normally, the recyclable display layer is used in a state after its full face is heated at the erasion temperature, namely, a state in which the entire recyclable display layer goes transparent. A specific portion of such a recyclable display layer is formed with a write area for writing or erasing symbol data 35.

A thermal head disposed in the card control section 39 for writing or erasing symbol data 35 on a recyclable card 26 is of high-temperature duration type allowing heating temperatures to be controlled at two steps.

The thermal head is heated to the write temperature for writing the symbol data 35 into the write area; to erase the symbol data 35 in the write area, the thermal head is heated to the erasion temperature and is controlled so as to locally trace the symbol data 35 only.

The card control section 39 writes visually the reduced image 23 used for the game play onto the surface of the recyclable card 26 at a player's request or at game play adjustment in response to an instruction from the game play control means 38, etc.

In the embodiment, we have discussed the gaming machine such as a slot machine for generating symbol data 21 for symbols on drums made of liquid crystal display units and changing symbols based on the symbol data 21, but the invention is not limited to it and can also be applied widely to gaming machines for making a game play progress with symbols, such as machines for changing facial expressions etc., of characters such as the heroes appearing in role playing games and shooting games placed on computer gaming machines.

Next, the function will be discussed.

The symbol data 21 is symbols displayed on the display screen of a slot machine, a pachinko slot machine, etc., or facial expressions of a character appearing on a game played on a computer gaming machine.

The image data 22 is input through the video camera 24 and output to the symbol change means 20. Also, the image data 22 previously stored on an image data base 25 may be read and output to the image construction section 34.

The face position specification lamp display section 33 specifies the direction in which the video camera 24 shoots a player. The player faces the video camera 24 attached to the gaming machine 10 in accordance with an instruction of the face position specification lamp display section 33 so that his or her facial expressions, etc., can be shot only from the front or from three directions of the front, left, and right.

A horizontal row arrangement of three lamps is used for the instruction on the face position specification lamp display section 33 of the embodiment. The player directs his or her face toward the direction in which the lamp goes on, whereby his or her facial expressions can be input as image data 22.

The image construction section 34 receives a game play control signal 40 from the game play control means 38 and a reduced image 23 from the line drawing creation section 30, generates symbol data 21, and outputs it to the composite screen display section 35.

In the embodiment, a liquid crystal display unit is used as the composite screen display section 35. It displays a composite image of a game play signal, for making a game play progress, generated by the game play signal generation section 36 and the symbol data 21, whereby the game play ability can be improved.

The image data base 25 may be located in the game play software section 37, for example. In the embodiment, stored image data 22, etc., can be used as the symbols or the facial expressions of characters, whereby the symbol data 21 can be used as symbols displayed on the display screen of a slot machine, pachinko slot machine, etc., and facial expressions of a character appearing on a game played on a computer gaming machine, improving the game play ability.

The image data 22 read from the image data base 25 is output to the game play signal generation section 36 and is subjected to predetermined data processing, then output to the image construction section 34 as a game play control signal 40. As the predetermined data processing for the read image data 22, the reduced image processing may be performed for outputting the resultant reduced image to the image construction section 34 as a game play control signal 40.

The symbol change means 20 of the embodiment performs line drawing processing for the image data 22 as reduced image processing for reducing the amount of the image data 22. The line drawing processing can be performed by combining line cut correction processing and contour detection processing. It is executed by the line cut correction section 31 and the contour detection section 32. A line drawing is used as the reduced image 23.

Density conversion processing for the optical density of the image data 22 is used as the line cut correction processing. It is performed mainly for enhancing contrast; for example, the density is converted for input image information so that a density histogram with a density on the horizontal axis and the number of pixels having the density on the vertical axis, is made flat, whereby contrast is enhanced. Differential enhancement processing and edge detection processing are used as the contour detection processing, whereby a binary image is generated from the image data 22 for use as the reduced image 23. For example, a two-dimensional structure extraction coding method for coding by extracting image edge information can be used. Contours can be extracted from the image information according to the edge information for separating the image into contours and other smooth portions for coding. The coding algorithm of Sketch Based Coding by Carlsson can be used as coding based on contours. In the embodiment, the reduction processing refers to conversion of an object to a sufficiently perceptible image while lessening the data capacity.

When the symbol change means 20 performs line drawing processing by contour enhancement for the image data 22, the image data 22 is binary-1-bit coded, for example, according to a predetermined image density threshold value. The data amount of analog image data such as a video signal or digital image data, for example, coded as 16 bits can be reduced.

Since line drawing processing is performed for the image data 22 as reduced image processing for reducing the amount of the image data 22, the memory scale can be made as small as a small-capacity image memory of about several 10 kB and a small-capacity video memory of about several 10 kB.

The amount of 1-frame image data is about several 10 kB and the transfer time of about several ms is enough to transfer 1-frame of symbol data from the image memory to the video memory. Even if game play progress is made using moving pictures as with a slot machine or a computer gaming machine with a liquid crystal display unit, the data transfer time does not limit the moving picture display speed and can be shortened.

Further, high-speed image processing and high-speed data transmission technique are not required to synchronize the transfer time with the moving picture display speed, reducing machine costs.

Necessary items on the recyclable card 26 can be visually and repeatedly recorded and erased. The recyclable card 26 is inserted into the card slot (not shown) made in the card control section 39 for use.

The card control section 39 visually writes the reduced image 23 used for the game play onto the recyclable display layer formed on the surface of the recyclable card 26 in response to an instruction from the game play control means 38, etc., at a player's request or at game play adjustment, whereby the player can record his or her facial expressions used for the game play, the facial expressions of the character, or the like on the surface of the recyclable card 26; the game play ability can be improved. The recyclable card 26 is inserted into the card slot (not shown) made in the card control section 39 for use. To write the symbol data 35 onto the recyclable display layer of the recyclable card 26, first the thermal head attached to the card control section 39 is adjusted to the write temperature (100 or higher) and the write area is heated by the thermal head to form digits, shapes, etc. Then, only the heated portion of the write area is made cloudy and the symbol data 35 is written.

On the other hand, to erase the symbol data 35, the thermal head is adjusted to the erasion temperature (70–95° C.) and only the symbol data 35 is locally traced and heated by the thermal head. The symbol data 35 heated at the erasion temperature goes transparent or invisible; the card thus becomes recyclable.

The gaming machine according to the embodiment performs line drawing processing for the image data 22 as reduced image processing for reducing the amount of the image data 22, thus the data capacity can be further reduced and processing can be performed with a small-capacity image memory of about several 10 kB and a small-capacity video memory of about several 10 kB; the gaming machine of the embodiment can hold and display a larger amount of symbol data than another gaming machine having the same storage capacity.

The amount of 1-frame image data can be reduced to about several 10 kB and the transfer time of about several ms becomes enough to transfer 1-frame symbol data from the image memory to the video memory. Even if game play progress is made using moving pictures as with a slot machine or a computer gaming machine with a liquid crystal display unit, the data transfer time does not limit the moving picture display speed, the game play operation speed is not impaired, and the game play ability can be improved.

Likewise, high-speed image processing and high-speed data transmission techniques are not required to synchronize the transfer time with the moving picture display speed, reducing machine costs.

Next, an embodiment of an input image management system for using an input image for a security system will be discussed.

In the embodiment, player's image information input for each gaming machine is sent to a management system for managing the gaming house and the management system manages the image information of the player playing a game for each gaming machine. An abnormal condition detector may further be provided for each gaming machine for informing the management system of an abnormal condition when it detects the condition. For example, if a player performs such an illegal act as guiding metal balls into a winning hole with a magnet while playing a game, the illegal act can be detected if a magnet detector is provided as the abnormal condition detector.

The embodiment will be discussed with reference to FIGS. 17–23.

Figure 17:
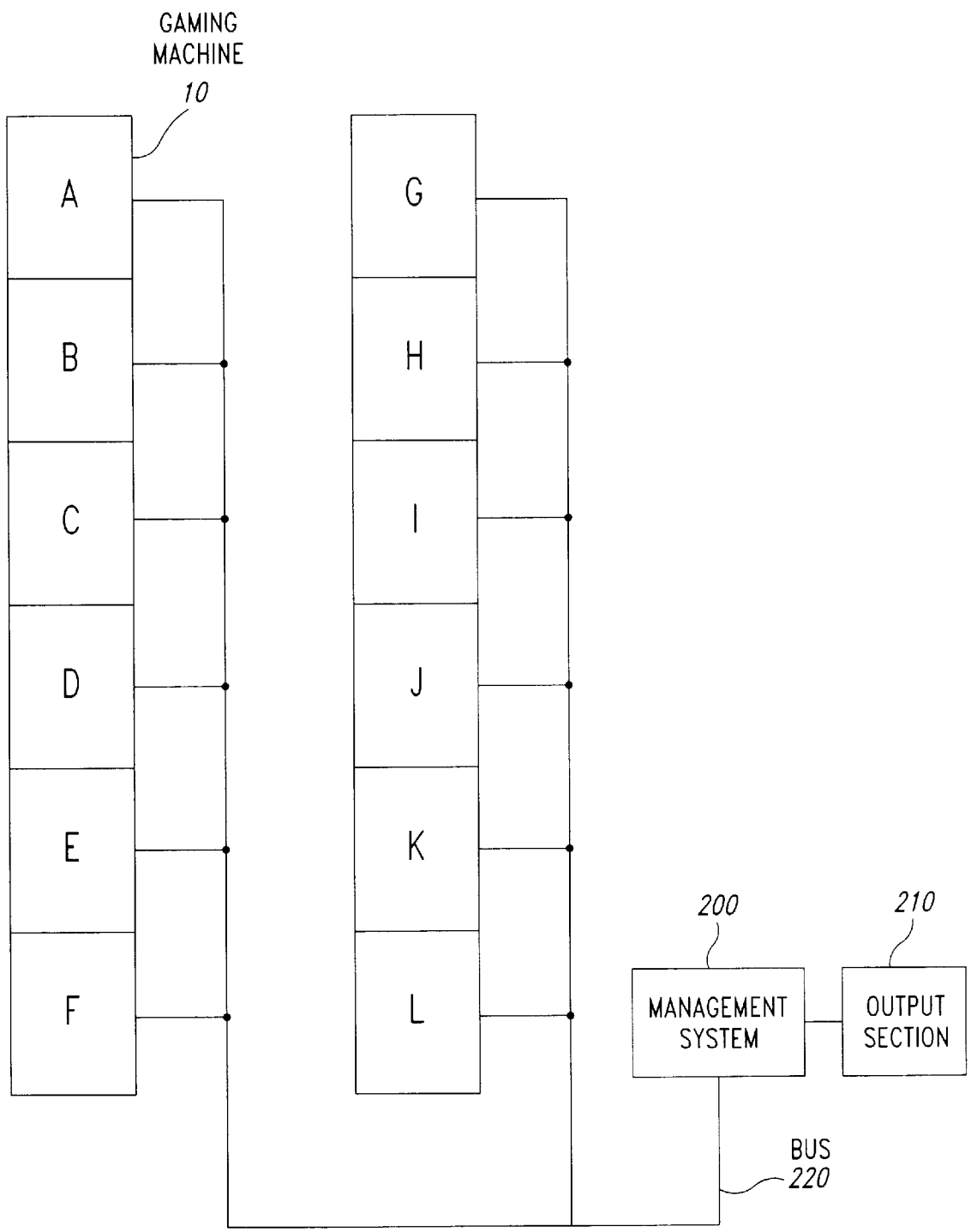
FIG. 17 is a block diagram of a gaming house when the invention is applied to a security system in another embodiment.

FIG. 17 is a general block diagram of the input image management system in the embodiment, wherein gaming machines 10A–10L are connected to a management system 200 by a bus in a gaming house having the gaming machines 10A–10L. Each of the gaming machines 10A–10L is a gaming machine comprising an image input unit such as a camera section 121 as shown in FIG. 1 or 2 discussed above and player's appearances can be input as image information. Each of the gaming machines 10A–10L further includes an image transmission section 425 for transmitting image information resulting from image processing and is connected to an image processing unit 420 for processing an input image as shown in FIG. 4 and is connected to the management system 200 via a bus line 220 as shown in FIG. 17. The management system 200 is connected to each of the gaming machines 10A–10L via the bus line 220 for receiving image information from each of the gaming machines.

Figure 22:
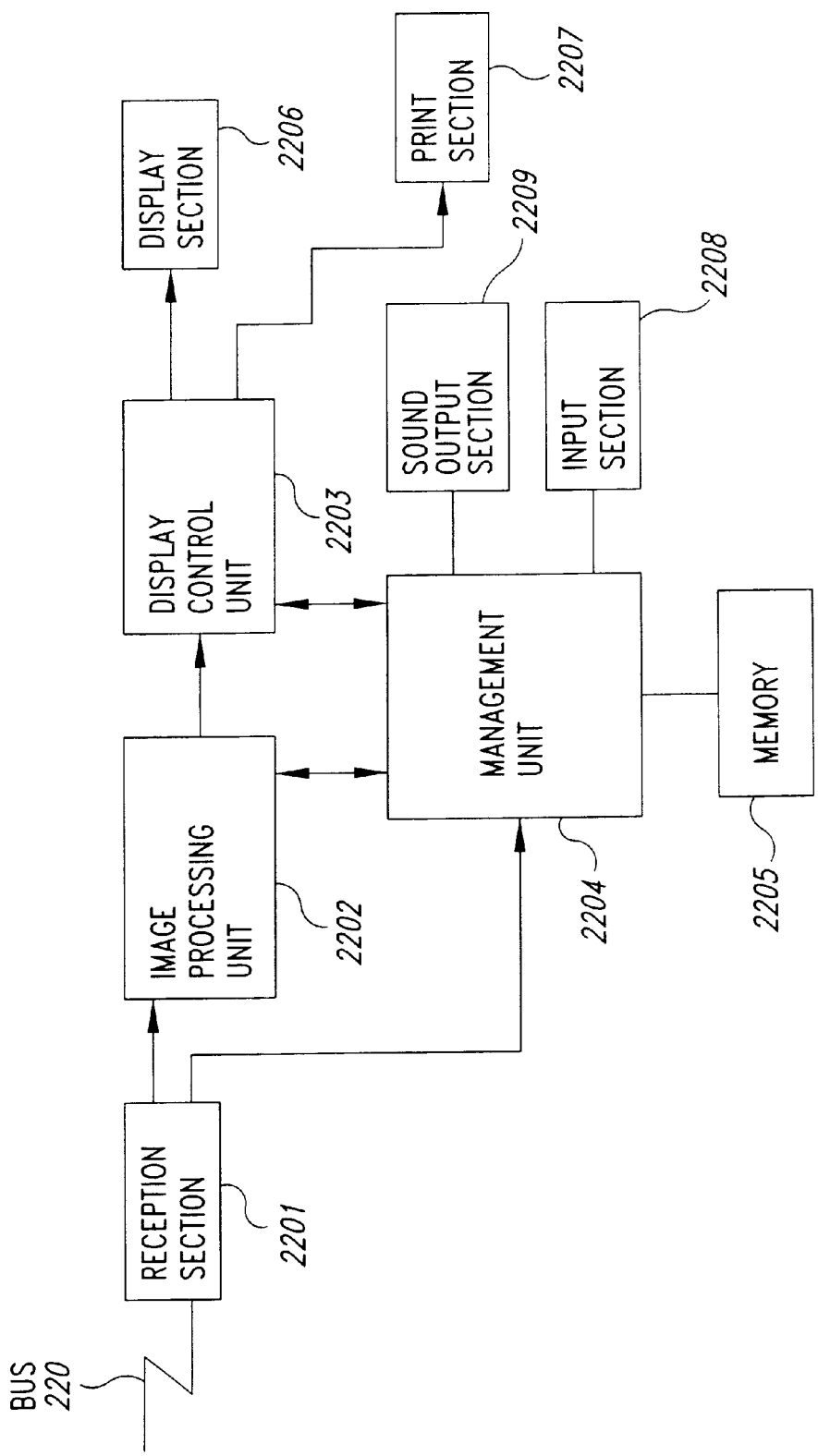
FIG. 22 is a block diagram when the invention is applied to the security system in the embodiment.

As shown in FIG. 22, a schematic block diagram, the management system 200 comprises a reception section 2201 connected to the gaming machines 10A–10L via the bus line 220 for receiving transmitted image information, an image processing unit 2202 for performing image processing for the image information received at the reception section 2201, a display control unit 2203 for controlling display of the image information processed by the image processing unit 2202, a management unit 2204 for managing the image information transmitted from the gaming machines, a display section 2206 for displaying the image information under the control of the display control unit 2203, a print section 2207 for printing out the image information, a memory 2205 for storing the image information, and an input section 2208 such as a keyboard. The management system 200 assigns identification information (image number) to each of image information icons transmitted from the gaming machines for managing the image information for each gaming machine.

Image information can be transferred between the transmission sections 425 of the gaming machines and the reception section 2201 of the management system in accordance with a predetermined protocol. For example, the management system 200 can use a polling method to poll the gaming machines through the reception section 2201, and when new image information is input (for example, image information input after the image input specification button 122 shown in FIG. 1 is pressed as described above can be regarded as new input image information), the gaming machine can respond to the polling with the new input image information. In this case, each gaming machine can further include a memory for storing the image information. A protocol such as CSMA/CD (Carrier Sense Multiple Access with Collision Detection) system may also be used.

The image processing unit 420 of each gaming machine may perform reduction or compression processing for the image information to be transmitted. The image information is thus sent out from the gaming machines.

The management system 200 receives the transmitted image information at the reception section 2201. The received image information is sent to the image processing unit 2202, which then decompresses the image information if it is compressed. Further, the image processing unit 2202 may apply reduction processing to the image information if necessary. The management unit 2204 adds image information identification information to the image information processed by the image processing unit 2202 and the image information is stored in the address location of the memory 2205 corresponding to the image information identification information. If the image information is compressed, it may be stored as it is in the memory 2205 through the management unit 2204 without performing image processing for the image information by the image processing unit 2002.

The management unit 2204 of the management system 200 comprises a management table 2210 as shown in FIG. 23. In FIG. 23, the management table 2210 is provided for each gaming machine for storing image information identification information (image number) of a player playing a game at the corresponding gaming machine. The player's image information identification information can be assigned serial numbers in the information transmission order, for example, and can be cleared every day. The information sent out from each gaming machine may include the number of game play media used for game play for each player at the gaming machine (input to the gaming machine), which will be hereinafter referred to as the number of input balls, the number of game play media paid out to each player for winning game plays from the gaming machine, which will be hereinafter referred to as the number of output balls, and the game start time and end time for each player in addition to the image information. For the number of input balls and the number of output balls, detection signals detected by detectors such as the media flow-out detection sensor for detecting paying-out of game play media and the media detection sensor for detecting input of game play media shown in FIG. 4 can be counted and the counts can be sent. For the game start time and end time, as described above, the time at which the image input specification button 122 shown in FIG. 1 is pressed may be regarded as the start time and the time at which the adjustment switch 107 shown in FIG. 4 is pressed may be regarded as the end time. Alternatively, if the radiation section 2122 and the light receiving section 2123 are provided as shown in FIG. 8, they detect the presence of a player, whereby the game play start time and end time can be found.

Each gaming machine may further include an illegal act detector for detecting an illegal act. The illegal act detector is a detector as described in International Laid-Open No. W092/09344 pamphlet, wherein a gaming machine is provided with a metal sensing matrix sensor for detecting an abnormal path of input game play media of metallic body, whereby an illegal act can be detected. The illegal act is, for example, an act of intentionally bending the motion direction of a metallic body with a magnet, etc., from the outside for guiding the metallic body into a winning hole. If such an illegal act detector is provided and detects an illegal act, the management system is informed that the illegal act has been detected. When receiving the information indicating the illegal act detection, the management system can display or print out the identification information of the gaming machine and the image information of the looks of the player playing a game at the gaming machine together with the information indicating the illegal act.

Next, a gaming machine management method in the management system 200 will be discussed with reference to FIGS. 18–21, which show display screen examples of the display section 2206 in the management system 200.

Figure 18:
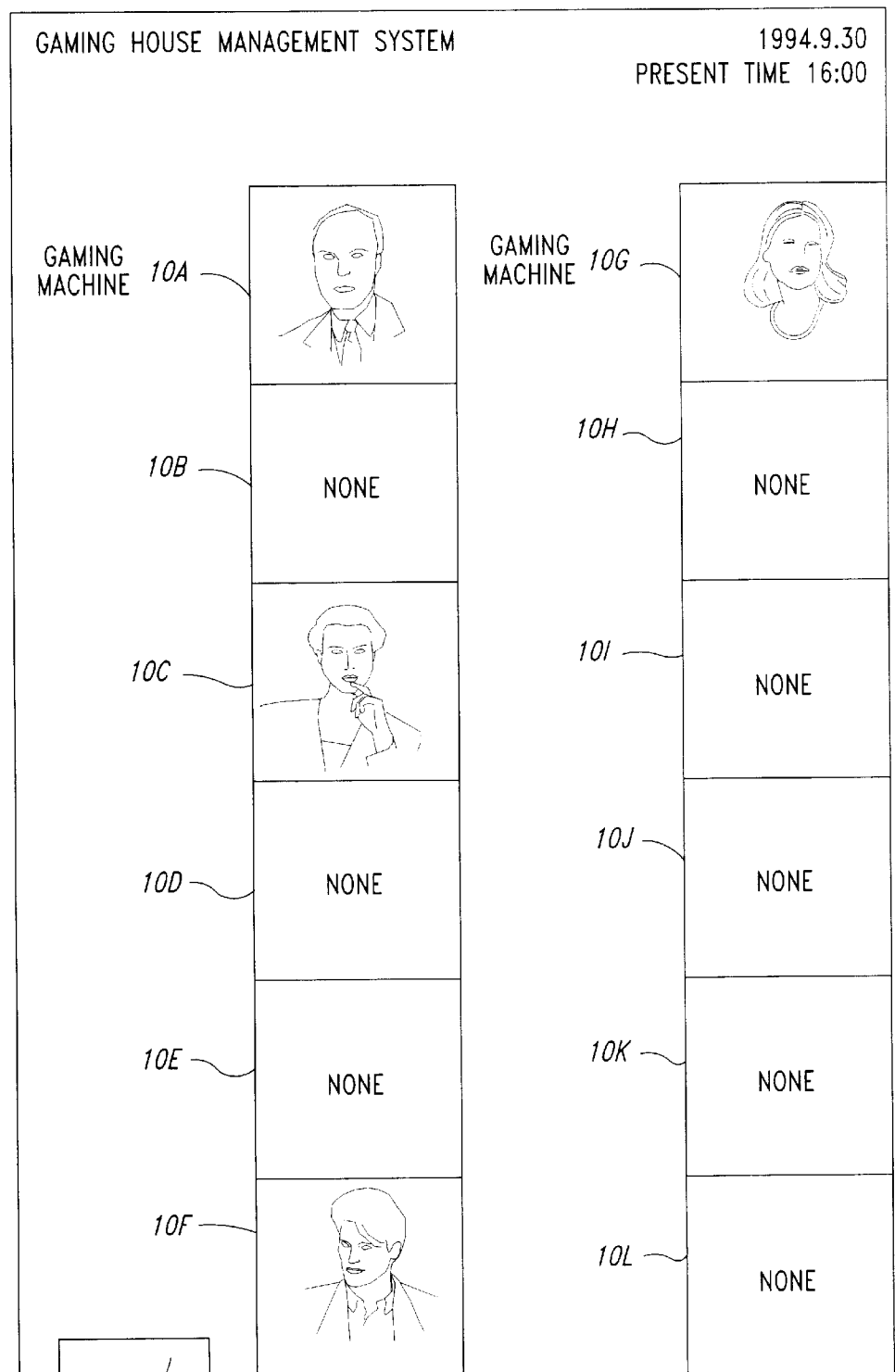
Figure 19:
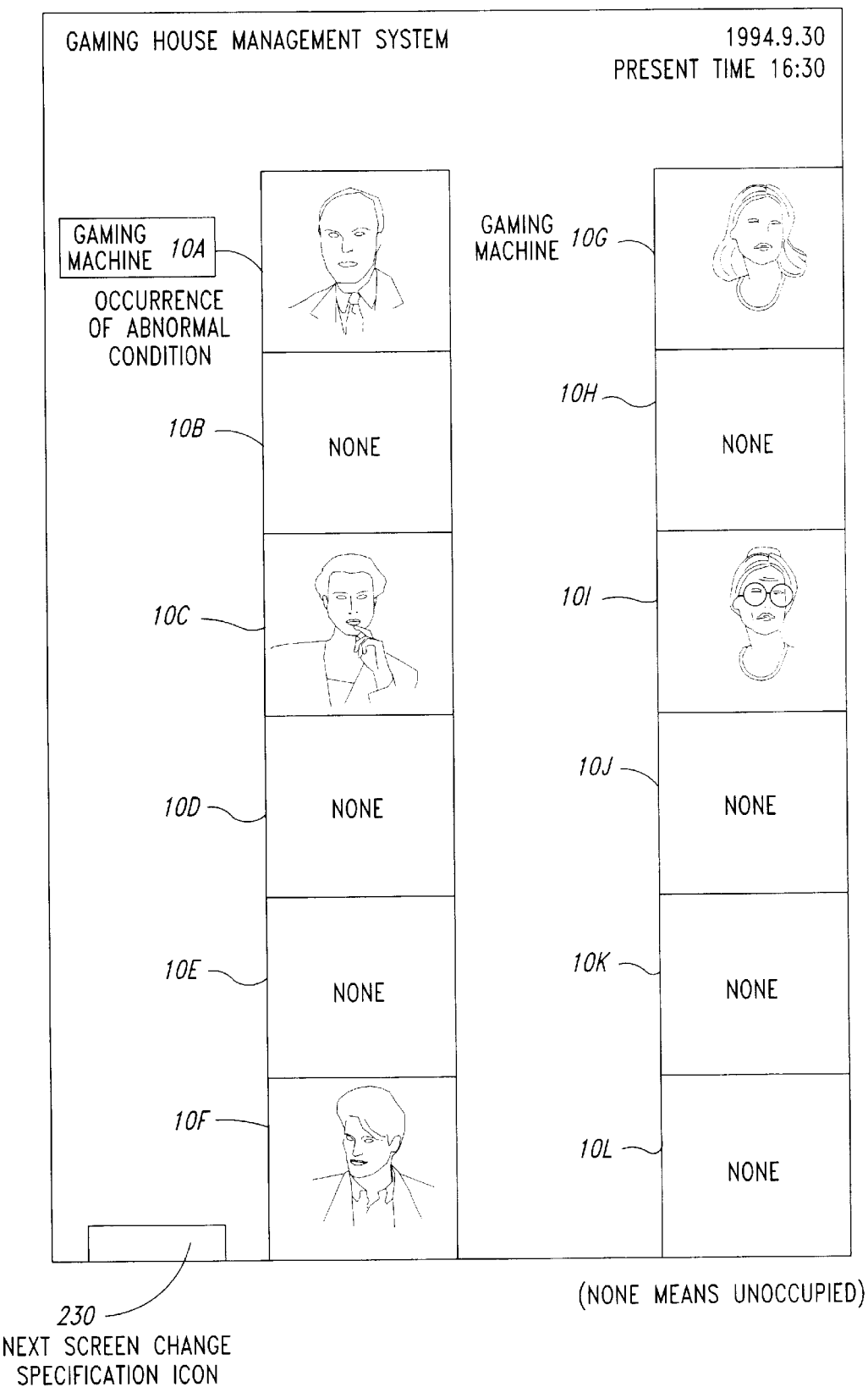

As shown in FIGS. 18 and 19, the use conditions of the gaming machines at the present point in time in the gaming house and image information of players using the gaming machines are displayed on the display section 2206. For example, when the gaming machine 101 is not used at the time 16:00 as shown in FIG. 18, if new image information is transmitted from the gaming machine and received at the reception section 2201 of the management system 200, the image information of the player at the gaming machine 101 is displayed as shown in FIG. 19 through the display processing unit 2202, the management unit 2204, and the display control unit 2203, whereby gaming machine players can be identified each time.

A touch panel as the input section 2208 may be disposed on the display front of the display section 2206. In this case, for example, as shown in FIGS. 18 and 19, a next screen change specification icon 230 or the like is provided and if the next screen change specification icon 230 on the screen is touched, the current screen can be changed to the next predetermined screen. In the embodiment, for example, if the next screen change specification icon 230 is touched after the identification information of a gaming machine such as the gaming machine 10A is touched, a change can be made to screen display showing the use conditions of the gaming machine 10A as shown in FIG. 20. In the figure, the player's image information, the game play time, the number of input balls, the number of output balls, an abnormal condition flag, etc., can be displayed for each player as the use conditions of the gaming machine 10A on the day, whereby the players playing games can be identified together with the use conditions of each gaming machine.

Further, when the management system is informed that an illegal act has been detected, the management unit 2204 can change the display color of the identification information of the gaming machine at which the illegal act has been performed, and display a message "OCCURRENCE OF ABNORMAL CONDITION" so as to indicate the illegal act, as shown in FIG. 19. If the management system further includes a sound output section 2209 as shown in FIG. 22, a predetermined alarm sound may be output.

Figure 21:
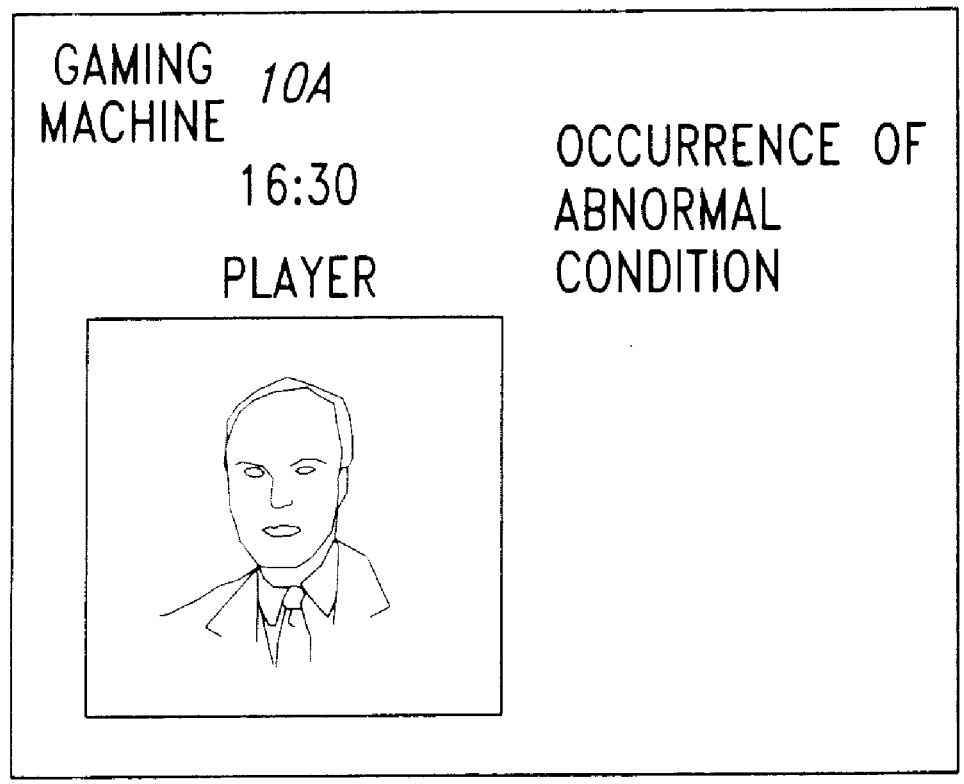

Further, when an illegal act has occurred, image information showing the appearances of the player performing the illegal act may be shown on an enlarged scale on the screen, together with the identification information of the gaming machine, as shown in FIG. 21. In this case, the management unit 2204 causes the image processing unit 2202 to perform enlargement processing for the image information of the current player at the gaming machine where the illegal act has been performed, and the display control unit 2203 to display the information on the display section 2206. The print section 2207 may make a hard copy of the display information for output.

When an illegal act has occurred, the image information of the current player at the gaming machine where the illegal act has been performed is displayed. Therefore, the gaming house manager can identify the player performing the illegal act based on the image information. Thus, input images can be managed intensively for preventing crime.

As we have discussed, according to the invention, image information can be input and displayed instead of gaming image information, whereby the player can have a sense in taking part in a game and can enjoy playing a game. Therefore, the hall having the gaming machines of the invention can also expect an increase in the number of players.

The invention can be applied to a security system by managing image information.

We claim:

1. An image display gaming apparatus for displaying an image of a plurality of symbols and for a player to play a slot machine type game when said plurality of symbols match a predetermined symbol combination, comprising:

an insertion section through which a storage medium, on which image information is stored, is inserted;

a read section for reading the image information from said storage medium inserted through said insertion section;

a game execution section for executing said slot machine type game;

a display section having a display screen for displaying an image;

a display control section for a control for displaying at least a game image information concerning games, including said symbols;

detection means for detecting that a plurality of images match the predetermined combination during a game execution by said game execution section; and a game image information storage for storing the game image information including at least image information of a group of symbols that are used in executing the slot machine type game, wherein said display control section controls to sequentially read image information of any one of the symbols from said image information of a group of symbols stored in said image information storage and to display the image information on said display screen of said display section during the game execution, and when it is detected by said detection means that said plurality of symbols match said predetermined combination, the image information read out from said storage medium by said read section is displayed on said display section, instead of the symbols that match the predetermined combination.

2. The image display gaming apparatus as in claim 1 wherein said display control section displays a plurality of betting lines on the display screen of said display section for indicating positions on which a combination of symbols may be generated causing a player to win a game, and areas are provided respectively to an edge of the betting lines for displaying images read from said storage medium.

3. The image display gaming apparatus as in claim 2 wherein said display control section receives a selection of said betting lines and displays the image read from said storage medium in the areas for displaying the image respectively to an edge of at least one of the betting lines having been selected.

4. A storage medium issuing apparatus for issuing storage media used in an image display gaming apparatus being provided in a gaming house, for displaying an image of a plurality of symbols and for a player to play a slot machine type game, the player winning the game when said plurality of symbols match a predetermined symbol combination, said apparatus comprising:

image pickup apparatus for picking up an image of an object;

image processing means for performing an image processing on image information of the image picked up by said image pickup apparatus so as to change the image information to be displayed as a symbol used in said image display gaming apparatus;

write means for writing the image information, on which the image processing have been performed, into a storage medium prepared in advance; and issuing means for issuing the storage medium on which the image information has been written.

5. The image display gaming apparatus as claimed in claim 4 wherein said write means visibly writes on a surface of said storage medium the image information having been processed by said image processing means.

6. The image display gaming apparatus as claimed in claim 5 wherein said storage medium issuing apparatus performs writing said image information on said storage medium so as to be stored visibly thereon and deleting said image information therefrom, said writing and deleting being repeatedly performed on said storage medium.

7. The storage medium issuing apparatus as claimed in claim 4 wherein said image pickup apparatus is a CCD (Charge Coupled Device) camera.

8. The storage medium issuing aparatus as claimed in claim 7 wherein said CCD camera has an automatic focusing function.

9. The storage medium issuing apparatus as claimed in claim 4 wherein said storage medium issuing apparatus further includes a specific-image display section for displaying the image information.

10. The storage medium issuing apparatus as claimed in claim 4 wherein said storage medium issuing apparatus further includes a print section for printing out the image information which has been picked up by said image pickup apparatus.

11. The storage medium issuing apparatus as claimed in claim 10 wherein said storage medium further includes an area for storing visually discernible information concerning a holder of said storage medium, the visually discernible infomation including the image information.

12. The storage medium issuing apparatus as claimed in claim 4 wherein said storage medium has:

a substrate comprising an image information storing area; and a fixed image display section being disposed on at least one surface of said substrate for fixedly displaying visualized information of the image information.

13. The storage medium issuing apparatus as claimed in claim 4, further comprising means for accepting an instruction from an insertion section to take out the storage medium inserted in said insertion section and for discharging the storage medium from said insertion section.

* * * * *